United States Patent
Amaro et al.

(10) Patent No.: US 9,737,546 B2
(45) Date of Patent: Aug. 22, 2017

(54) SMALL MOLECULES TO ENHANCE P53 ACTIVITY

(71) Applicant: THE REGENTS OF THE UNIVERSITY OF CALIFORNIA, Oakland, CA (US)

(72) Inventors: Rommie E. Amaro, San Clemente, CA (US); Roberta Baronio, Oxford (GB); Ozlem Demir, San Diego, CA (US); Peter Kaiser, Irvine, CA (US); Richard H. Lathrop, Irvine, CA (US); Seyedey-Faezeh Salehi-Amin, Pasadena, CA (US); Christopher D. Wassman, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/910,976

(22) PCT Filed: Aug. 9, 2014

(86) PCT No.: PCT/US2014/050458
§ 371 (c)(1),
(2) Date: Feb. 8, 2016

(87) PCT Pub. No.: WO2015/021456
PCT Pub. Date: Feb. 12, 2015

(65) Prior Publication Data
US 2016/0193214 A1 Jul. 7, 2016

Related U.S. Application Data

(60) Provisional application No. 61/864,441, filed on Aug. 9, 2013.

(51) Int. Cl.
| | | |
|---|---|---|
| A61K 31/429 | (2006.01) |
| A61K 31/538 | (2006.01) |
| A61K 31/4184 | (2006.01) |
| A61K 31/47 | (2006.01) |
| A61K 31/4155 | (2006.01) |
| A61K 31/416 | (2006.01) |
| A61K 31/44 | (2006.01) |
| A61K 31/4704 | (2006.01) |
| A61K 31/472 | (2006.01) |
| A61K 45/06 | (2006.01) |
| C07D 213/75 | (2006.01) |
| C07D 215/38 | (2006.01) |
| C07D 217/24 | (2006.01) |
| C07D 231/54 | (2006.01) |
| C07D 265/36 | (2006.01) |
| C07D 405/04 | (2006.01) |
| C07D 513/04 | (2006.01) |

(52) U.S. Cl.
CPC .......... *A61K 31/538* (2013.01); *A61K 31/416* (2013.01); *A61K 31/4155* (2013.01); *A61K 31/4184* (2013.01); *A61K 31/429* (2013.01); *A61K 31/44* (2013.01); *A61K 31/47* (2013.01); *A61K 31/472* (2013.01); *A61K 31/4704* (2013.01); *A61K 45/06* (2013.01); *C07D 213/75* (2013.01); *C07D 215/38* (2013.01); *C07D 217/24* (2013.01); *C07D 231/54* (2013.01); *C07D 265/36* (2013.01); *C07D 405/04* (2013.01); *C07D 513/04* (2013.01)

(58) Field of Classification Search
USPC ............. 514/230.5, 309, 313, 352, 366, 406
See application file for complete search history.

(56) References Cited

U.S. PATENT DOCUMENTS

2008/0085890 A1 4/2008 Tsou et al.
2009/0054417 A1 2/2009 Michellys et al.

FOREIGN PATENT DOCUMENTS

EP 0549348 A1 6/1993

OTHER PUBLICATIONS

Webb (Journal of Bioorganic and Medicinal Chemistry; 11 (2003) 77-85).*
McCarthy (Nature Reviews Cancer; May 31, 2013; Research highlights).*
(Amaro, et al., 2008) Amaro RE, Baron R, McCammon JA, An improved relaxed complex scheme for receptor flexibility in a computer-aided drug design. Journal of computer-aided molecular design. 2008;22(9):693-705. Epub Jan. 15, 2008. doi: 10.1007/s10822-077-9159-2. PubMed PMID: 18196463; PubMed Central PMCID: PMC2516539.
(Amaro & Li, 2010) Amaro RE, Li WW. Emerging methods for emsemble-based vrtual screening. Curr Top Med Chem. 2010:10(1):3-13. Review.

(Continued)

*Primary Examiner* — Pancham Bakshi
(74) *Attorney, Agent, or Firm* — Berliner & Associates

(57) ABSTRACT

A method of enhancing p53 activity of a p53 mutant polypeptide is provided. The method includes interacting a compound to an open L1/S3 binding site of the p53 mutant polypeptide, where the p53 activity of the p53 mutant polypeptide is enhanced in the presence of the compound. Compounds were identified from databases of compounds for virtual drug screening. Methods of screening for compounds that enhance p53 activity by binding to the open L1/S3 binding site, and methods of treatment using the identified compounds, are also provided.

2 Claims, 9 Drawing Sheets

(56) References Cited

OTHER PUBLICATIONS (Baronio, et al., 2010) Baronio R, Danzinger SA, Hall LV, Salmon K, Hatfield GW, Lathrop RH, Kaiser P. All-Codon Scanning Identifies p53 cancer rescue mutations. Nucleic Acids Res. Nov. 1, 2010:38(20):7079-88. Epub Jun. 25, 2010.
(Basse, et al., 2010) Basse N, Kaar JL, Settanni G, Joerger AC, Rutherford TJ, Fersht AR. Toward the rational design of p53-stabilizing drugs: probing the surface of the oncogenic Y220C mutant. Chemistry & biology. 2010:17(1):46-56. Epub Feb. 10, 2010. doi: 10.1016/j.chembiol.2009.12.011. PubMed PMID: 20142040.
Beraza & Trautwein, 2007, Beraza N, Trautwein C. Restoration of p53 function: a new therapeutic strategy to induce tumor regression? Hepatology. Jun. 2007;45(6):1578-9.
(Bichutskly, et al., 2007) Bichutskly VY, Colman R, Brachmann RK, Lathrop RH. Heterogeneous Biomedical Database Integration Using a Hybrid Strategy: A p53 Cancer Research Database. Cancer informatics. 2007;2:277-87.
(Boeckler, et al., 2008) Boeckler FM, Joerger AC, Jaggi G, Rutherford TJ, Veprintsev DB, Fersht AR, Targeted rescue of a destabilized mutant of p53 by an in silico screened drug. Proc Natl Acad Sci U S A. Jul. 29, 2008;105(30):10360-5. Epub Jul. 23, 2008.
(Brown, et al., 2009) Brown CJ, Lain S, Verma CS, Fersht AR, Lane DP. Awakening guardian angels: drugging the p53 pathway. Nat Rev Cancer. Dec. 2009:9(12):862-73. Review.
(Bykov, et al., 2002) Bykov VJ, Issaeva N, Shilov A, Hultcrantz M, Pugacheva E, Chumakov P, Bergman J, Winman KG, Med. Mar. 2007;8(3):282-8.
(Bykov, et al., 2005) Bykov VJ, Issaeva N, Zache N, Shilov A, Hultcrantz M, Bergman J, Selivanova G, Wiman KG. Reactivation of mutant p53 and induction of apoptosis in human tumor cells by maleimide analogs. J Biol Chem. Aug. 26, 2005;280(34):30384-91. Epub Jul. 1, 2005.
(Canadillas,et al., 2006) Canadillas JM, Tidow H, Freund SM, Rutherford TJ, Ang HC, Fersht AR. Solution structure of p53 core domain: structural basis for its instability. Proc Natl Acad Sci U S A. Feb. 14, 2006;103(7):2109-14. Epub Feb. 6, 2006.
(Canals, et al., 2005) Canals A, Purciolas M, Ayamami J, Coll M, The Anticancer agent ellipticine unwinds DNA by intercalative binding in an orientation parallel to base pairs. Acta Crystallogr D Biol Crystallogr. Jul. 2005;61(pt 7):1009-12. Epub Jun. 24, 2005.
(Danzinger, et al., 2006) Danzinger SA, Swamidass SJ, Zeng J, Dearth LR, Lu Q, Chen JH, Cheng J, Hoang VP, Saigo H, Luo R, Baldi P, Brachmann RK, Lathrop RH, Functional census of mutation sequences spaces: the examples of p53 cancer rescue mutants. IEEE/ACM Trans Comput Biol Bioinform. Apr.-Jun. 2006;3(2):114-25.
(Danziger, et al., 2007) Danziger SA, Zeng J, Wang Y, Brauchmann, RK, Lathrop RH. Choosing where to look next in a mutation sequence space: Active Learning of informative p53 cancer rescue mutants. Bioinformatics. Jul. 1, 2007:23(13):i104-14.
(Danziger, et al., 2009) Danziger SA, Baronio R, Ho L, Hall LV, Salmon K, Hatfield GW, Kaiser P, Lathrop RH, Predicting positive p53 cancer rescue regions using Most Informative Positive (MIP) active learning. PLoS Comput Biol. Sep. 2009;5(9):e1000498. Epub Sep. 4, 2008.
(Daura, et al., 1998) Daura X, Jaun B, Seebach D, van Gunsteren WF, Mark AE. Reversible peptide folding in solution by molecular dynamics simulation. J Mol Biol, 1998. 280(5): p. 925-32.
(Daura, et al., 1999) Daura X GK, Jaun B, Seebach D, van Gunsteren WF, et al., Peptide folding: When simulation meets experiment. Angew Chem-Int Edit. 1999:38:236-40.
(Demir, et al., 2011) Demir O, Baronio R, Salehi F, Wassman CD, Hall L, Hatfield GW, Chamberlin R, Kaiser P, Lathrop RH, Amaro RE. Ensemble-based computational approach discriminated functional activity of p53 cancer and rescue mutants. PLoS computational biology. 2011;7(10):e1002238. Epub Oct. 27, 2011. doi 10.1371/journal.pcbi.1002238. PubMed PMID: 22028641; PubMed Central PMCID: PMC3197647.
(Demma, et al., 2004) Demma MJ, Wong S, Maxwell E, Dasmahapatra B. CP-31398 restores DNA-binding activity to mutant p53 in vitro but does not affect p53 homologs p63 and p73. J Biol Chem. Oct. 29, 2004;279(44):45887-96. Epub Aug. 11, 2004.
(Demma, et al., 2010) Demma M, Maxwell E, Ramos R, Liang L, Li C, Hesk D, Rossman R, Mallams A, Doll R, Liu M, Seidel-Dugan C, Bishop WR, Dasmahaptra B, SCH529074, a small molecule activator of mutant p53, which binds p53 DNA binding domain (DBD), restores growth-suppressive function to mutant p53 and interrupts HDM2-mediated ubiquitination of wild type p53. J Biol Chem. Apr. 2, 2010:285(14):10198-212. Epub Feb. 2, 2010.
(Durrant, et al., 2010) Durrant JD, Hall L, Swift RV, Landon M, Schnaufer A, Amaro RE. Novel napthalene-based inhibitors of Trypanosoma brucei RNA editing ligase 1. PLos Negl Trap Dis. Aug. 24, 2010:4(8):e803.
(Farhat, et al., 2014) Farhat A, Malecki E, Bonaterra GA, Rothlein D, Wolf M, Schmitt J, Rosepeyer H, Kinscherf R. Cytostatic/cytoxic effects of 5-fluorouridine nucleolipids on colon, hepatocellular, and renal carcinma cells: in vitro identification of a potential cytotoxic multi-anticancer drug. Chem Biodivers. Mar. 2014:11(3):469-82. doi: 10.1002/cbdv.201300347.
(Fleuret, 2004) Fleuret F. Fast binary feature selection with conditional mutual information. J Mach Learn Res. 2004;5:1531-55. PubMed PMID: ISI:000236328400005.
(Foster, et al., 1999) Foster BA, Coffey HA, Morin MJ, Rastinejad F. Pharmacological rescue of mutant p53 conformation and function. Science. Dec. 24, 1999;286(5449):2507-10.
(Friedler, et al., 2002) Friedler A, Hansson LO, Veprintsev DB, Freund SM, Rippin TM, Nikolova PV, Proctor MR, Rudiger S, Fersht AR. A peptide that binds and stabilizes p53 core domain: chaperone strategy for rescue of oncogenic mutants. Proc Natl Acad Sci U S A. Jan. 22, 2002;99(2):937-42. Epub Jan. 8, 2002.
(Friedler, et al., 2004) Friedler A, DeDecker BS, Freund SM, Blair C, Rudiger S, Fersht AR. Structural distortion of p53 by the mutation R249S and its rescue by a designed peptide: implications for "mutant conformation". J Mol Biol. Feb. 6, 2004;336(1):187-96.
(Garufi, et al., 2013) Garufi A, Trisciuoglio D, Porru M, Leonetti C, Stoppacciaro A, D'Orazi V, Avantaggiati M, Crispini A, Pucci D, D'Orazi G. A fluorescent curcumin-based Zn(II)-complex reactivates mutant (R175H and R273H) p53 in cancer cells. J Exp Clin Cancer Res. Oct. 7, 2013;32:72. doi: 10.1186-1756-9966-32-72.
(González-Billalbeitia, et al., 2014) González-Billalabeitia E, Seitzer N, Song SJ, Song MS, Patnaik A, Liu XS, Epping MT, Papa A, Hobbs RM, Chen M, Lunardi A, Ng C, Webster KA, Signoretti S, Loda M, Asara JM, Nardella C. Colhessy JG, Cantley LC, Pandolfi PP. Vulnerabilities of PTEN-TP53-Deficient Prostate Cancers to Compound PARP-P13K Inhibition. Cancer Discov. Aug. 2014;4(8):896-904. doi: 10.1158/2159-8290.CD-13-0230. Epub May 27, 2014.
(Hara, et al., 2006) Hara T, Durell SR, Myers MC, Appella DH. Probing the Structural requirements of peptoids that inhibit HDM2-p53 interactions. J Am Chem Soc. Feb. 15, 2006;128(6):1995-2004.
(Hess, et al., 2008) Hess B, Kutzner C, van der Spoel D, Lindahl E. GROMACS 4: Algorithms for Highly Efficient, Load-Balanced, and Scalable Molecular Simulation. J Chem Theory Comput 2006; 4(3): 435-447.
(Hock & Vousden, 2012.) Hock AK, Vousden KH. Tumor Suppression by p53: fall of the triumvirate? Cell. Jun. 8, 2012;149(6):1183-5. doi: 10.1016/j.coll.2012.05.024.
(Horvath, Marcou, & Varnek, 2013) Horvath D, Marcou G, Varnek A. Do not hesitate to use Tversky—and other hints for successful active analogue searches with feature count descriptors. Journal of chemical information and modeling. 2013. Epub Jun. 5, 2013. doi: 10.1021/c1400106g. PubMed PMID: 23731336.
(Issaeva, et al., 2003) Issaeva N, Friedler A, Bozko P, Wiman KG, Fersht AR, Selivanova G. Rescue of mutants of the tumor suppressor p53 in cancer cells by designed peptide. Proc Natl Acad Sci U S A. Nov. 11, 2003;100(23):13303-7. Epub Oct. 31, 2003.
(Issaeva, et al., 2004) Issaeva N, Bozko P, Enge M, Protopopova M, Verhoef LG, Masucci M, Pramanik A, Selivanova G. Small mol-

(56) References Cited

OTHER PUBLICATIONS ecule RITA binds to p53, blocks p53-HDM-2 interaction and activities p53 function in tumors. Nat Med. Dec. 2004; 10(12):1321-8. Epub Nov. 21, 2004.
(Jain, 2003) Jain AN. Surflex: fully automatic flexible molecular docking using a molecular similarity-based search engine. Journal of medicinal chemistry. 2003;46(4):499-511. Epub Feb. 7, 2003. doi: 10.1021/jm020406h. PubMed PMID: 12570372.
(Jain, 2007) Jain AN. Surflex-Dock 2.1: robust performance from ligand energetic modeling, ring flexibility, and knowledge-based search. Journal of computer-aided molecular design. 2007;21(5):281-306. Epub Mar. 28, 2007. doi: 10.1007/s10622-007-9114-2. PubMed PMID: 17387436.
(Kaar, et al., 2010) Kaar JL, Basse N, Joerger AC, Stephens E, Rutherford TJ, Fersht AR. Stabilization of mutant p53 via alkylation of cysteines and effects on DNA binding. Protein Sci. Dec. 2010;19(12):2267-78. doi: 10.1002/pro.507.
(Karimi, et al., 2010) Karimi M, Conserva F, Mahmoudi S, Bergman J, Wiman KG, Bykov VJ. Extract from Asteraceae Brachylaena ramiflora induces apoptosis preferentially in mutant p53-expressing human tumor cells. Carcinogenesis. Jun. 2010;31(6):1045-53. Epub Apr. 28, 2010.
(Kohn, et al., 1975) Kohn KW, Waring MJ, Glaubiger D, Friedman CA. Intercalative binding of ellipticine to DNA. Cancer Res. Jan. 1975;35(1):71-6.
(Kravchenko, et al., 2008) Kravchenko JE, Ilyinskaya GV, Komarov PG, Agapova LS, Kochetkov DV, Strom E, Frolova EI, Kovriga I, Gudkov AV, Feinstein E, Chumakov PM. Small-molecule RETRA supresses mutant p53-bearing cancer cells through a p73 dependent salvage pathway. Proc Natl Acad Sci U S A. Apr. 29, 2008;105(17):6302-7. Epub Apr. 18, 2008.
(Lambert, et al., 2009) Lambert JM, Gorzov P, Veprintsev DB, Soderqvist M, Sergenback D, Bergman J, Fersht AR, Hainaut P, Wiman KG, Bykov VJ, PRIMA-1 reactivates mutant p53 by covalent binding to the core domain. Cancer Cell. May 5, 2009;15(5):376-68.
(Le Guilloux, et al., 2009) Le Guilloux V, Schmidtke P, Tuffery P. Fpocket: an open source platform for ligand pocket detection. BMC Bioinformatics. Jun. 2, 2009;10:168.
(Li, et al., 2011) Li TI, Kon N, Jiang L, Tan M, Ludwig T, Zhao Y, Baer R, Gu W. Cell. Jun. 8, 2012:149(6):1269-83. doi: 10.1016/j.cell.2012.05.026. Tumor supression in the absence of p53-mediated cell-cycle arrest, apoptosis, and senescence.
(Lindahl, et al., 2001) Lindahl E, Hess B, van der Spoel D, GROMACS 3.0: A package for molecular simulation and trajectory analysis. J Mol Mo. 2001. 7: p. 306-317.
(Liu, et al., 2013) Liu X, Wicken R, Joerger AC, Chuckowree IS, Amin J, Spencer J, Fersht AR. Small molecule induced reactivation of mutant p53 in cancer cells. Nucleic Acids Res. Jul. 1, 2013;41(12):6034-44 doi: 10.1093/nar/gkt305. Epub Apr. 29, 2013.
(Malecka, et al., 2009) Malecka KA, Ho WC, Marmorstein R. Crystal structure of a p53 core tetramer bound to DNA. Oncogene. Jan. 22, 2009;28(3):325-33. Epub Nov. 3, 2008.
(Maslon & Hupp, 2010) Maslon MM, Hupp TR. Drug discovery and mutant p53. Trends Cell Biol. Sep. 2010;20(9):542-55. Epub Jul. 24, 2010. Review.
(Metri, et al., 2013) Metri PK, Naz S, Kondaiah P, Prasad KR, MPK-09, a Small Molecule Inspired from Bioactive Styryllactone Restores the Wild-Type Function of Mutant p53. ACS Chem Biol. Apr. 26, 2013. [Epub ahead of print].
(Myers, et al., 2005) Myers MC, Wang J, Iera JA, Bang JK, Hara T, Saito S, Zambetti GP, Appella DH. A new family of small molecules to probe the reactivation of mutant p53. J Am Chem Soc. May 4, 2005;127(17):6152-3.
(Olivier, et al., 2002) Olivier M, Eeles R, Hollistein M, Khan MA, Harris CC, Hainaut P. The IARC TP53 database new online mutation analysis and recommendations to users. Hum Mutat. Jun. 2002;19(6):607-14.
(Olivier, et al., 2009) Olivier M, Petitjean A, Marcel V, Pétré A, Mounawar M, Plymoth A, de Fromentel CC, Hainaut P. Recent advances in p53 research: an interdisciplinary perspective. Cancer Gene Ther Jan. 2009;16(1):1-12. Epub Sep. 19, 2008. Review.
(Oltersdorf, et al., 2005) Oltersdorf T, Elmore SW, Shoemaker AR, Armstrong RC, Augeri DJ, Belli BA, Bruncko M, Deckwerth TL, Dinges J, Hajduk PJ, Joseph MK, Kitada S, Korsmeyer SJ, Kunzer AR, Letai A, Li C, Mitten MJ, Nettesheim DG, Ng S, Nimmer PM, O'Connor JM, Oleksijew A, Petros AM, Reed JC, Shen W, Tahir SK, Thompson CB, Tomaselli KJ, Wang B, Wendt MD, Zhang H, Fesik SW, Rosenberg SH. An inhibitor of Bcl-2 family proteins induces regression of solid tumours. Nature, Jun. 2, 2005;435(7042):677-81. Epub May 15, 2005.
(Peltonen, et al., 2010) Peltonen K, Colis L, Liu H, Jäämaa S, Moore HM, Enbäck J, Laakkonen P, Vaahtokari A, Jones RJ, af Hällström TM, Laiho M. Identification of novel p53 pathway activating small-molecule compounds reveals unexpected similarities with known therapeutic agents. PLoS One. Sep 27, 2010;5(9);e12996.
(Peng, et al., 2003) Peng Y, Li C, Chen L, Sebti S, Chen J. Rescue of mutant p53 transcription function by ellipticine. Oncogene. Jul. 17, 2003;22(29):4478-87.
(Reddy, et al., 2004) Reddy NL, Hill J, Ye L, Fernandes PB, Stout DM. Identification and structure-activity relationship studies of 3-methylene-2-norbornanone as potent anti-proliferative agents presumably working through p53 mediated apoptosis. Bioorg Med Chem Lett. Nov. 15, 2004;14(22):5645-9.
(Reha, et al, 2002) Reha D, Kabeláč M, Ryjáček F, Sponer J, Sponer JE, Elstner M, Suhai S, Hobza P. Intercalators. 1. Nature of stacking interactions between intercalators (ethidium, daunomycin, ellipticine, and 4',6-diaminide-2-phenylindole) and DNA base pairs. Ab initio quantum chemical, density functional theory, and empirical potential study. J Am Chem Soc. Apr. 3, 2002;124(13):3386-76, Erratum in: J Am Chem Soc. May 7, 2003;125(18) following 5580.
(Rippin, et al., 2002) Rippin TM, Bykov VJ, Freund SM, Selivanova G, Wiman KG, Fersht AR. Characterization of the p53-rescue drug CP-31398 in vitro and in living cells. Oncogene. Mar. 28, 2002;21(14)1119-29.
(Ross, et al., 1978) Ross WE, Glaubiger DL, Kohn KW. Protein-associated DNA breaks in cells treated with adriamycin or ellipticine, Biochim Biophys Acta. Jun. 22, 1987;519(1):23-30.
(Selivanova, et al., 1997) Selivanova G, Iotsova V, Okan I, Fritsche M, Ström M, Groner B, Grafström RC, Wiman KG, Restoration of the growth suppression function of mutant p53 by a synthetic peptide derived from the p53 C-terminal domain. Nat Med. Jun. 1997;3(6):632-8.
(Selivanova & Wiman, 2007) Selivanova G, Wiman KG. Reactivation of mutant p53: molecular mechanisms and therapeutic potential. Oncogene. Apr. 2, 2007;26(15):2243-54.
(Shangary, et al, 2009) Shangary S. Wang S. Small-molecule inhibitors of the MDM2-p53 protein-protein ineracton to reactivate p53 function: a novel approach for cancer therapy. Annu Rev Pharmacol Toxicol. 2009;49:223-41, Review.
(Sharpless & DePinho, 2007) Sharpless NE, DePinho RA. Cancer biology: gone but not forgotten. Nature. Feb. 8, 2007;445(7128):606-7.
(Soussi & Béroud, 2001) Soussi T, Béroud C. Assessing TP53 status in human tumours to evaluate clinical outcome. Nat Rev Cancer. Dec. 2001:1(3):233-40. Review.
(Stoklosa & Golab, 2005) Stoklosa T, Gotab J. Prospects for p53-based cancer therapy. Acta Biochim Pol. 2005;52(2):321-8.
(Sutherland, et al., 2011) Sutherland HS, Hwang IY, Marshall ES, Lindsay BS, Denny WA, Gilchrist C. Joseph WR, Greenhalgh D, Richardson E, Kestell P, Ding A, Baguley BC. Therapeutic reactivation of mutant p53 protein by quinazoline derivatives. Invest New Drugs. Oct. 2012;30(5):2035-45, doi: 10.1007/s10637-011-9744-z. Epub Sep. 13, 2011.
(Trott & Olson, 2010) Trott O, Olson AJ, AutoDock Vina: improving the speed and accuracy of docking with a new scoring function, efficient optimization, and multithreading. J Comput Chem, Jan. 30, 2010;31(2):455-61.
(Valente, et al., 2013) Valente LJ, Gray DH, Michalak EM, Pinon-Hofbauer J, Egle A, Scott CL, Janie A, Strasser A. p53 efficiently suppresses tumor development in the complete absence of its cell-cycle inhibitory and proapoptotic effectors p21, Puma, and

(56) References Cited

OTHER PUBLICATIONS

Noxa, Cell Rep. May 30, 2013;3(5):1339-45. doi: 10.1016/j.celrep.2013.04.012, Epub May 9, 2013.
(Vassilev, et al., 2004) Vassiley LT, Vu BT, Graves B, Carvajal D, Podlaski F, Filipovic Z, Kong N, Kammlott U, Lukacs C, Klein C, Fotouhi N, Liu EA. In vivo activation of the p53 pathway by small-molecule antagonists of MDM2. Science. Feb. 6, 2004;303(5659):844-8 Epub Jan. 2, 2004.
(Ventura, et al., 2007) Ventura A, Kirsch DG, McLaughlin ME, Tuveson DA, Grimm J, Lintault L, Newman J, Reczek EE, Weissleder R, Jacks T. Restoration of p53 function leads to tumour regression in vivo, Nature, Feb. 8, 2007;445 (7128):661-5. Epub Jan. 24, 2007.
(Wang, et al., 2005) Wang Y, Hailey J, Williams D, Wang Y, Lipari P, Malkowski M, Wang X, Xie L, Li G, Saha D, Ling WL, Cannon-Carlson S, Greenberg R, Ramos RA, Shields R, Presta L, Brams P, Bishop WR, Pachter JA. Inhibition of insulin-like growth factor-I receptor (IGF-IR) signaling and tumor cell growth by a fully human neutralizing anti-IGF-IR antibody. Mol Cancer Ther Aug. 2005;4(8):1214-21.
(Wang & El-Deiry, 2008) Wang W, El-Deiry WS. Restoration of p53 to limit tumor growth. Curt Opin Oncol. Jan. 2008;20(1):90-6. Review.
(Wang, et al., 2009) Wang Y, Xiao J, Suzek TO, Zhang J, Wang J, Bryant SH. PubChem: a public information system for analyzing bioactivities of small molecules. Nucleic acids research. 2009;37(Web Server Issue):W623-33. Epub Jun. 6, 2009. doi. 10.1093/nar/gkp456. PubMed PMID: 19498078; PubMed Central PMCID: PMC2703903.
(Wassman, et al., 2013) Wassman CD, Baronio R, Demir O, Wallentine BD, Chen CK, Hall LV, Salehi F, Lin DW, Chung BP, Hatfield GW, Richard Chamberlin A, Luecke H, Lathrop RH, Kaiser P, Amaro RE. Computational identification of a transiently open L1/S3 pocket for reactivation of mutant p53. Nat Commun. 2013;4:1407. Epub Jan. 31, 2013. doi: 10.1038/ncomms2381.
(Weinmann, et al., 2008) Weinmann L, Wischhusen J, Demme MJ, Naumann U, Roth P, Dasmahapatra B, Weller M. A novel p53 rescue compound induces p53-dependent growth arrest and sensitises glioma cells to Apo2L/TRAIL-induced apoptosis, Cell Death Differ, Apr. 2008;15(4):718-29, dol: 10.1038/sj.cdd.4402301. Epub Jan. 18, 2008.
(Wilcken, et al., 2012) Wilcken R, Liu X, Zimmermann MO, Rutherford TJ, Fersht AR, Joerger AC, Boeckler FM. Halogen-Enriched Fragment Libraries as Leads for Drug Rescue of Mutant p53. Journal of the American Chemical Society. 2012;134(15):6810-8. Epub Mar. 24, 2012. doi: 10.1021/ja301056a. PubMed PMID; 22439615.
(Wiman, 2007) Wiman KG. Restoration of wild-type p53 function in human tumors: strategies for efficient cancer therapy. Adv Cancer Res. 2007;97:321-38. Review.
(Xue, et al, 2007) Xue W. Zender L, Miething C, Dickins RA, Hernando E, Krizhanovsky V, Cordon-Cardo C, Lowe SW. Senescence and tumour clearance is triggered by p53 restoration in murine liver carcinomas. Nature. Feb. 8, 2007;445(7128):656-60. Epub Jan. 24, 2007.
(Yu, et al., 2102) Yu, X., Vazquez, A., Levine, A. J. & Carpizo, D. R. Allele-Specific p53 Mutant Reactivation. Cancer cell 21, 614-625 (2012).
(Zache, et al., 2008) Zache N, Lambert JM, Rökaeus N, Shen J, Hainaut P, Bergman J, Wiman KG, Bykov VJ. Mutant p53 targeting by the low molecular weght compound STIMA-1 Mol Oncol. Jun. 2008;2(1)70-80. Epub Mar. 7, 2008.
(Zhao, et al., 2010a) Zhao CY, Szekely L, Bao W, Selivanova G. Rescue of p53 function by small-molecule RITA in cervical carcinoma by blocking E6-mediated degradation. Cancer Res. Apr. 15, 2010;70(8):372-81.
(Zhao, et al., 2010b) Zhao CY, Grinkevich VV, Nikulenkov F, Bao W, Selivanova G. Rescue of the apoptotic-inducing function of mutant p53 by small molecule RITA. Cell Cycle. May 2010;9(9):1847-55. Epub May 15, 2010.
PubChem: CID 5874196, Sep. 9, 2005.
Wassman, C. D., et al., "Computational identification of a transiently open LI/S3 pocket for reactivation of mutant p53" Nature communications, Epub. Jan. 29, 2013, vol. 4, No. 1407, pp. 1-9.
PCT Search Report and Written Opinion dated Jan. 20, 2015, issued in connection with PCT/US2014/050458 filed Aug. 9, 2014

\* cited by examiner

FIG. 1A

| Chemical Structure | | | | |
|---|---|---|---|---|
| SMILES | CC(=O)NN(C=C1)c2ccccc2C(=O)N(C1=O)c1ccccc1 | CCCCc1cc(o2)c(c[nH][nH])2c2ccc(o2)c(=O)NNC(=O)O | CC(C(=C)C(=C)C(=O)C(=C)OC(=C)N(C(=O)c1c2c(n[nH]1)CCC2 | CCOc1cc(ccc1O)yC=c1c(=O)n2c3ccccc3nc2s1 |
| Appr. LC50 | <50 μM | >50 μM | >50 μM | 30-40 μM |
| UCH ID | 3SZWF | 2SKKL | 2ZLSV | 32CTM |
| ZINC DB ID | ZINC32693825 | ZINC04555680 | ZINC00114983 | ZINC12421611 |

FIG. 1B

| Structure | SMILES | Activity | PDB | ZINC ID |
|---|---|---|---|---|
| (quinoline hydrazone with dihydroxyphenyl) | c1ccc2cc(ccc2c1)ccc(c1)/N/N=C/c1cccc(O)c1(O)O | 5-10 mM | 26RQZ | ZINC05688001 |
| (benzoxazinone chalcone with methoxyphenyl) | CCOc1ccccc1/C=C/C(=O)c1ccc2c(c1)NC(=O)CO2 | 1-5 µM | 27WT9 | ZINC07442756 |
| (naphthalene carboxamide – glycinamide – aminopyridine) | C(c1ccc(nc1)NC(=O)CNC(=O)c1ccc2cc2ccccc2c1 | 10 µM | 3SLWZ | ZINC27643621 |
| (nitrocinnamoyl benzimidazole) | c1ccc(c(c1)/C=C/C(=O)c1nc2ccccc2[nH])[N+](=O)O | 3-10 µM | 27UDP | ZINC07135644 |

FIG. 1C

| Structure | SMILES | Activity | ID | ZINC |
|---|---|---|---|---|
| (structure: indole-carbonyloxy-isoxazole amide) | Cc1cc(no1)NC(=O)[C@@H](C(O)Cc1ccc2c(c1)cc(c1)[nH]2)CC)C | 40-50 μM | 33AG6 | ZINC13985117 |
| (structure: indole-piperidine-acetamide-isoxazole) | Cc1cc(no1)NC(=O)CN1CCC(CC1)c1c[nH]c2c1cccc2 | >50 μM | 28NZ6 | ZINC08752625 |
| (structure: chromene carboxamide-benzamide) | CCNC(=O)c1cccc(c1)NC(=O)C1=Cc2ccccc2OC1 | 5-15 mM | 33BAZ | ZINC14095766 |
| (structure: quinazolinone with furan and cyanophenyl) | c1ccc2c(c1)C(=O)N(C(=O)N([C@@H](N2)c1ccc(cc1)C#N)Cc1ccco1 | 2-5 μM for G245S only | 27TGR | ZINC07112599 |

FIG. 2A

| Chemical Structure | | | | | |
|---|---|---|---|---|---|
| SMILES | c12n(c3cc1[C@@H](CCO2)C)ccc3)C(=O)CSc1[nH][cnn1 | c1(C(=O)Nc2cc(NC(=O)C)ccc2)oc(cc1)C | S(=O)(=O)(c1cc(ccc1Cl)Cl)Nc1c2c(c(c3)OC)cccn2 | c1(N(C(=N)C(=O)N)nc(c2c(n1)cccc2)C | C(=N)(C(=O)C)(Nc1nc2cc(n1)Ccc(c2)OC)NC(=O)C |
| Appr. LC50 | >50 μM | >50 μM | 10 μM | >50 μM | 20 μM |
| UCI ID | 39AND | 39CLD | 38UGS | 38TP2 | 38TYB |
| Chembridge DB ID | 7721985 | 7947715 | 5663715 | 5568132 | 5637261 |

US 9,737,546 B2

SMALL MOLECULES TO ENHANCE P53 ACTIVITY

STATEMENT REGARDING FEDERALLY SPONSORED RESEARCH OR DEVELOPMENT

This invention was made with Government support under Grant No. R01-CA-112560 and Grant No. DP2-OD-007237 received from the U.S. National Institutes of Health. The Government has certain rights in this invention.

BACKGROUND

Field of the Invention

The invention relates generally to p53 cancer mutants. More particularly, it relates to the use of small molecules to enhance p53 activity in p53 cancer mutants.

Related Art

1. Reactivation of p53 Cancer Mutants.

The tumor suppressor protein p53, called the "Guardian of the Genome," controls several central cellular tumor suppressor pathways, including cell cycle arrest, apoptosis (programmed cell death), and cellular senescence, in response to genomic damage and cellular or environmental stress. About half of all human cancers carry mutant p53, making p53 the most commonly mutated protein in human cancers. Most p53 cancer mutants exhibit a single missense mutation, which results in full-length p53 protein with a single amino acid change (Olivier, et al., 2002, 2009).

Pharmaceutical reactivation of p53 cancer mutants (p53 "cancer rescue") is a long-held goal of cancer therapy. The presence of full-length but mutated p53 in so many human cancers holds the promise of a novel cancer treatment strategy—small molecule drugs that favor or stabilize the wild-type conformation of p53, restore p53 function to cancer mutants, and reactivate p53 tumor suppressor pathways, thus shrinking or killing the tumor (Soussi & Beroud, 2001; Selivanova & Wiman, 2007; Sharpless & DePinho, 2007; Ventura, et al., 2007; Wiman, 2007; Xue, et al., 2007; Wang & El-Deiry, 2008; Brown, et al., 2009).

1.1. Challenges Facing Pharmaceutical Reactivation of p53 Cancer Mutants.

Challenges are summarized succinctly by a passage from a recent (2010) review article:

"In contrast to stimulating wt-p53 function, reactivation of a mutant and inactive protein as a therapeutic strategy might appear insurmountable if not naïve." (Maslon & Hupp, 2010, p. 549).

Challenges include: (1) a diverse variety of p53 cancer mutants and mechanisms; (2) the marginal stability of p53 at physiological temperatures; (3) insufficient understanding of p53 dynamics or flexibility; (4) elusive knowledge about the precise molecular mechanisms that reactivate p53 cancer mutants; (5) a paucity of p53 reactivation drug leads; (6) the novelty and difficulty of designing drugs to stabilize protein conformation instead of to modulate enzyme or signaling activity; and (7) a lack of sophisticated computational analysis tools to guide p53 biological and pharmaceutical discovery.

1.2. Current Small Molecule Approaches that Target p53 Reactivation.

Small molecule approaches that target p53 reactivation fall into several classes, including: (1) approaches that appear to intercalate small molecules into DNA, or otherwise cause DNA damage or DNA conformational change, and thereby perhaps increase the activation stimulus acting on p53 (Kohn, et al., 1975; Ross, et al., 1978; Foster, et al., 1999; Demma, et al., 2004; Reha, et al., 2002; Rippin, et al., 2002; Peng, et al., 2003; Canals, et al., 2005; Peltonen, et al., 2010); (2) approaches that appear to employ peptides or peptide-mimetics that bind to p53 (Selivanova, et al., 1997; Friedler, et al., 2002, 2004; Issaeva, et al., 2003); (3) approaches that appear to employ small molecules that bind covalently to p53 via cysteine alkylation (Bykov, et al., 2002, 2005; Beraza & Trautwein, 2007; Zache, et al., 2008; Lambert, et al., 2009; Kaar, et al., 2010; Karimi, et al., 2010); (4) approaches that appear to employ small molecules that bind non-covalently to p53 (Yu, et al., 2012; Zhao, et al., 2010ab); and (5) approaches that appear to employ small molecules or peptides that block p53 proteolysis or otherwise interact with p53 binding partners and so increase p53 protein abundance or activity (Wang, et al., 2005; Hara, et al., 2006; Vassilev, et al., 2004; Oltersdorf, et al., 2005; Kravchenko, et al., 2008; Shangary, et al., 2009; Demma, et al., 2010). However, these categories are often uncertain, imprecise, or overlapping.

SUMMARY

In one aspect, a method of enhancing p53 activity of a p53 mutant polypeptide is provided. The method includes interacting the p53 mutant polypeptide with at least one compound listed in any of FIGS. 1-2, or a tautomer, derivative or pharmaceutically acceptable salt thereof, or a combination thereof, where the p53 activity of the p53 mutant polypeptide is enhanced in the presence of the at least one compound as compared to the activity of the p53 mutant polypeptide in the absence of the at least one compound. In some embodiments, the at least one compound is compound ZINC database ID ZINC07135644 of FIG. 1, or compound Chembridge database ID 5663715 of FIG. 2, or a combination thereof.

In another aspect, a method of treating cancer in a subject in need of such treatment is provided. The method includes administering to the subject an effective amount of at least one compound listed in any of FIGS. 1-2, or a tautomer, derivative or pharmaceutically acceptable salt thereof, or a combination thereof, where cancer cells of the cancer express a p53 mutant polypeptide whose p53 activity is enhanced in the presence of the at least one compound as compared to the activity of the p53 mutant polypeptide in the absence of the at least one compound.

In some embodiments of the method: a) the at least one compound can be compound ZINC database ID ZINC07135644 of FIG. 1, or compound Chembridge database ID 5663715 of FIG. 2, or a combination thereof; b) the treating can further include administering one or more chemotherapeutic agents, one or more cancer therapies, or a combination thereof, to the subject; or c) any combination of a) and b).

In a further aspect, a compound listed in any of FIGS. 1-2, or a tautomer, derivative or pharmaceutically acceptable salt thereof, is provided for use as a medicament. In some embodiments, the compound is compound ZINC database ID ZINC07135644 of FIG. 1, or compound Chembridge database ID 5663715 of FIG. 2

In another aspect, a compound listed in any of FIGS. 1-2, or a tautomer, derivative or pharmaceutically acceptable salt thereof, is provided for use in the treatment of a cancer having cells that express a p53 mutant polypeptide whose activity is enhanced in the presence of the compound as compared to the activity of the p53 mutant polypeptide in the absence of the compound. In some embodiments, the compound is compound ZINC database ID ZINC07135644 of FIG. 1, or compound Chembridge database ID 5663715 of FIG. 2.

In a further aspect, a composition is provided for use in the treatment of a cancer having cells that express a p53 mutant polypeptide whose activity is enhanced in the presence of the composition as compared to the activity of the p53 mutant polypeptide in the absence of the composition. In this method, the composition includes at least one compound listed in any of FIGS. 1-2, or a tautomer, derivative or pharmaceutically acceptable salt thereof, or a combination thereof.

In some embodiments of the method: a) the at least one compound is compound ZINC database ID ZINC07135644 of FIG. 1, or compound Chembridge database ID 5663715 of FIG. 2, or a combination thereof; b) the composition further includes a pharmaceutically acceptable carrier; c) the at least one compound is two or more of the compounds listed in any of FIGS. 1-2, or tautomers, derivatives or pharmaceutically acceptable salts thereof, or a combination thereof; or d) any combination of a)-c).

In another aspect, a method of enhancing p53 activity of a p53 mutant polypeptide is provided. The method includes interacting a compound with an open L1/S3 binding site of the p53 mutant polypeptide, where the open L1/S3 binding site is defined by the criteria set forth in Table 1, and the p53 activity of the p53 mutant polypeptide is enhanced in the presence of the compound as compared to the activity of the p53 mutant polypeptide in the absence of the compound.

In some embodiments of the method, the compound is not: PRIMA-1; PRIMA-1-MET; methylene quinuclidinone; STIMA-1; 3-methylene-2-norbornanone; MIRA-1; MIRA-2; MIRA-3; NSC319725; NSC319726; CP-31398; SCH529074; PARP-PI3K; 5,50-(2,5-furandiyl)bis-2-thiophenemethanol; MPK-09; Zn-curc or curcumin-based Zn(II)-complex; P53R3; a (2-benzofuranyl)-quinazoline derivative; a nucleolipid derivative of 5-fluorouridine; a derivative of 2-aminoacetophenone hydrochloride; PK083; PK5174; or PK7088. In some embodiments, the compound is one or more compounds listed in any of FIGS. 1-2, or tautomers, derivatives or pharmaceutically acceptable salts thereof, or a combination thereof.

In a further aspect, a compound that interacts with an open L1/S3 binding site of a p53 mutant polypeptide is provided for use as a medicament. In embodiments the open L1/S3 binding site is defined by the criteria set forth in Table 1, and the p53 activity of the p53 mutant polypeptide is enhanced in the presence of the compound as compared to the activity of the p53 mutant polypeptide in the absence of the compound. In some embodiments, the compound is for use in the treatment of a cancer whose cancer cells express the p53 mutant polypeptide. In some embodiments, the compound is compound ZINC database ID ZINC07135644 of FIG. 1, or compound Chembridge database ID 5663715 of FIG. 2.

In another aspect, a method of screening for a compound that enhances p53 activity of a p53 mutant polypeptide is provided. The method includes performing a virtual screen of a test compound for interaction with an open L1/S3 binding site of a p53 polypeptide as defined by the criteria set forth in Table 1. In some embodiments, the method further includes measuring p53 activity of a p53 mutant polypeptide in the presence and absence of the test compound.

In a further aspect, a method of treating cancer in a subject in need of such treatment is provided. The method includes administering an effective amount of a compound to the subject, where cancer cells of the cancer express a p53 mutant polypeptide whose p53 activity is enhanced in the presence of the compound as compared to the activity of the p53 mutant polypeptide in the absence of the compound. In the method, the compound interacts with an open L1/S3 binding site of the p53 mutant polypeptide, the open L1/S3 binding site being defined by the criteria set forth in Table 1. In some embodiments of the method: a) the compound is not: PRIMA-1; PRIMA-1-MET; methylene quinuclidinone; STIMA-1; 3-methylene-2-norbornanone; MIRA-1; MIRA-2; MIRA-3; NSC319725; NSC319726; CP-31398; SCH529074; PARP-PI3K; 5,50-(2,5-furandiyl)bis-2-thiophenemethanol; MPK-09; Zn-curc or curcumin-based Zn(II)-complex; P53R3; a (2-benzofuranyl)-quinazoline derivative, a nucleolipid derivative of 5-fluorouridine; a derivative of 2-aminoacetophenone hydrochloride; PK083; PK5174; or PK7088; b) the compound is a compound listed in any of FIGS. 1-2, or a tautomer, derivative or pharmaceutically acceptable salt thereof; c) the treating further comprises administering at least one other compound listed in any of FIGS. 1-2, or a tautomer, derivative or pharmaceutically acceptable salt thereof, or combination thereof; d) the treating further comprises administering one or more chemotherapeutic agents, one or more cancer therapies, or a combination thereof, to the subject; or e) any combination of a)-d)

Some embodiments of the invention include 24 small molecule drug leads demonstrated to enhance p53 activity in p53 cancer mutants (FIGS. 1-3). Some embodiments include the high value of novel cancer therapeutic drugs. Compounds described herein were not previously proposed to enhance p53 activity in p53 cancer mutants. Some embodiments reduced the initial 1,738,752 compounds in the ZINC Leads Now database down to the 16 compounds shown in FIG. 1, a reduction of 108,672-fold. Some embodiments reduced the initial 448,532 compounds in the Chembridge Express Pick Library 2012 database compounds down to the 8 compounds shown in FIG. 2, a reduction of 56,066-fold. Some embodiments include the biological data in FIG. 3. In some embodiments, the small number of compounds can be purchased from chemical supply companies, then assayed using the methods disclosed herein.

BRIEF DESCRIPTION OF THE DRAWINGS

For a more complete understanding of the present invention, reference is now made to the following descriptions taken in conjunction with the accompanying drawings and tables, in which:

FIGS. 1A-1D ("FIG. 1") provide a list of sixteen compounds that enhance p53 activity, selected as described below from the Zinc Leads Now database, version of January, 2011. These sixteen compounds correspond to FIG. 3A and are described below in section 4. The compounds disclosed in FIGS. 1A-1D are intended to encompass all tautomers and pharmaceutically acceptable salts, as defined below.

FIGS. 2A-2B ("FIG. 2") provide a list of eight compounds that enhance p53 activity, selected as described below from the Chembridge Express Pick Library 2012 database. These eight compounds correspond to FIG. 3B and are described below in section 4. The compounds disclosed in FIGS. 2A-2B are intended to encompass all tautomers and pharmaceutically acceptable salts, as defined below.

FIG. 3A is a graph of reactivation activities of various compounds. Saos-2 cells expressing no p53 ($p53^{null}$), or expressing one of the cancer mutants p53-R175H or p53-G245S, were cultured for 3 days in the presence of different concentrations of compounds that had been selected from the Zinc Leads Now database, version of January, 2011, by the computational methods described below. The p53 reactivation compounds shown correspond to FIG. 1. Cell numbers were measured using the CellTiter-Glo® reagent. Results are shown for the highest compound concentration (max. 200 μM) that did not significantly affect cell proliferation of the parental Saos-2 ($p53^{null}$) cells: PRIMA-1 (50 μM); stictic acid (37 μM); 35ZWF, 25KKL, 22LSV, 28NZ6, and 27TGR (100 μM); 32CTM (40 μM); 26RQZ and 32LDE (10 μM); 33AG6 (200 μM); 33BAZ (60 μM); 27VFS (20 μM); and 32JCB (150 μM). Data are presented as the standard error of the mean (n=3). Note that as of this writing eight compounds have been tested on the R175H mutant only (32CTM, 28NZ6, 27TGR, 27VFS, 35LWZ, 36EB5, 32LDE, and 32JCB).

FIG. 3B is a graph of reactivation activities of various compounds. Experimental conditions are as in FIG. 3A, but compounds were selected from the Chembridge Express Pick Library 2012 database, by the computational methods described below. The p53 reactivation compounds shown correspond to FIG. 2. Results are shown for the highest compound concentration (max. 80 μM) that did not significantly affect cell proliferation of the parental Saos-2 ($p53^{null}$) cells: 39AND, 38TP2, 39CME, and 38WHV (60 μM); 39CLD (80 μM); 38UGS (10 μM); 38TYB (20 μM); and 39GGC (3 μM).

FIG. 3C is a graph of dose response curves for compounds 33BAZ and 27UDP using four different p53 cancer mutants: R175H, G245S, R248W, and R273H. Experimental conditions are as in FIG. 3A.

FIG. 3D is a panel of graphs of broad spectrum activity for four other compounds using four different p53 cancer mutants: R175H, G245S, R248W, and R273H. Experimental conditions are as in FIG. 3C, but a single dose was assayed: 27VFS (20 μM), 35LWZ (50 μM), 27WT9 (10 μM), and 26RQZ (10 μM).

FIG. 3E is a panel of micrograph visualizations of compound-induced cell death in $p53^{null}$ cells (first row) or cells expressing p53 cancer mutants (R175H and G245S, second and third rows, respectively). Cells were cultured with vehicle (DMSO) or the compounds indicated (concentrations as above) for 24 h and then micrographs were taken.

FIG. 3F is a panel of graphs of compound-activated expression of the p53 target genes MDM2 and NOXA in cells expressing the p53 cancer mutant G245S. Cells as above were exposed to the compounds indicated for 8 h before RNA was isolated. MDM2 and NOXA mRNA was monitored by qRT-PCR and normalized to actin mRNA.

FIG. 3G is a panel showing compound-activated expression of the p53 target gene p21 in cells expressing p53 cancer mutants. Cells as above were exposed to the compounds indicated for 12 h. Expression of p21 was monitored by immunoblotting. Equal loading was confirmed by amidoblack staining.

FIG. 4A shows that Cys124 is occluded in the human p53 crystal structure 1TSR-B. FIG. 4B shows that the structure extracted from molecular dynamics (MD) simulation of the p53-R273H cancer mutant system revealed new "breathing" structural topography near Cys124 within the range of normal solution dynamics. In our MD simulations, Cys124 is "open" about 5-8% of the time (Wassman, et al., 2013) depending on the system.

DETAILED DESCRIPTION

The following application is incorporated by reference herein: U.S. Provisional Patent Application No. 61/864,441, filed on Aug. 9, 2013.

The term "reactivation" compound, "reactivating" compound, "rescue" compound, or "cancer rescue" compound, refers herein to any compound capable of enhancing p53 activity in one or more p53 cancer mutants, as determined using one or more of the biological or chemical methods described in this application, or any other method known to those of skill in the art.

The term "enhance" or "enhancing" refers herein to the ability to increase the p53 activity level of one or more p53 cancer mutants to an activity level greater than the baseline p53 activity level expressed by the p53 cancer mutant in the absence of any modification or small molecule interaction. Thus, this term includes increasing the p53 activity level of a p53 cancer mutant by any amount, even if below full p53 'native' activity; or increasing the p53 activity level of the p53 cancer mutant back to 'native' p53 activity level (restoration' or 'reactivation'); or increasing the p53 activity level of the p53 cancer mutant to a level above that found in the 'native' p53 protein. A compound that enhances the activity of one or more p53 cancer mutants also may be called a p53 reactivation compound, a p53 reactivating compound, a p53 rescue compound, or a p53 cancer rescue compound.

The term "chemical derivative" as used herein means a compound obtained by varying the chemical structure of an original compound, for example, via a simple reaction or the substitution of an atom, moiety, or functional group of the original compound. Such derivatives of a compound may involve the insertion, deletion, or substitution of one or more atoms, moieties, or functional groups without fundamentally altering the essential scaffold of the original compound. Examples of such atoms, moieties, or functional groups include, but are not limited to, methyl, ethyl, propyl, butyl, hydroxyl, ester, ether, acyl, alkyl, carboxyl, halide, ketyl, carbonyl, aldehyde, alkenyl, azide, benzyl, fluoro, formyl, amide, imide, phenyl, nitrile, methoxy, phosphate, phosphodiester, vinyl, thiol, sulfide, or sulfoxide atoms, moieties, or functional groups. Many methods for creating a chemical derivative from an original compound are known in the art.

Figure 1D:
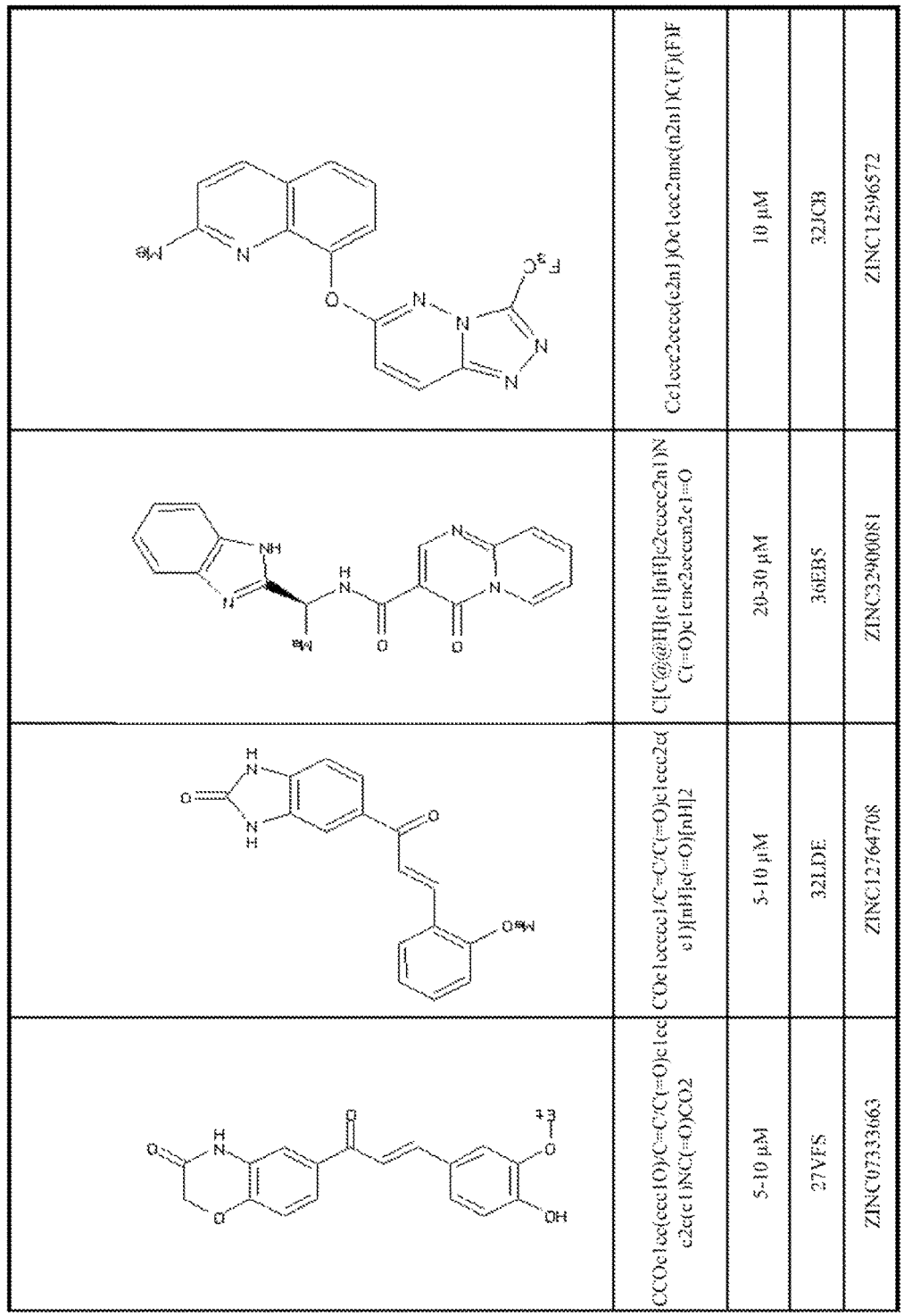
Figure 2B:
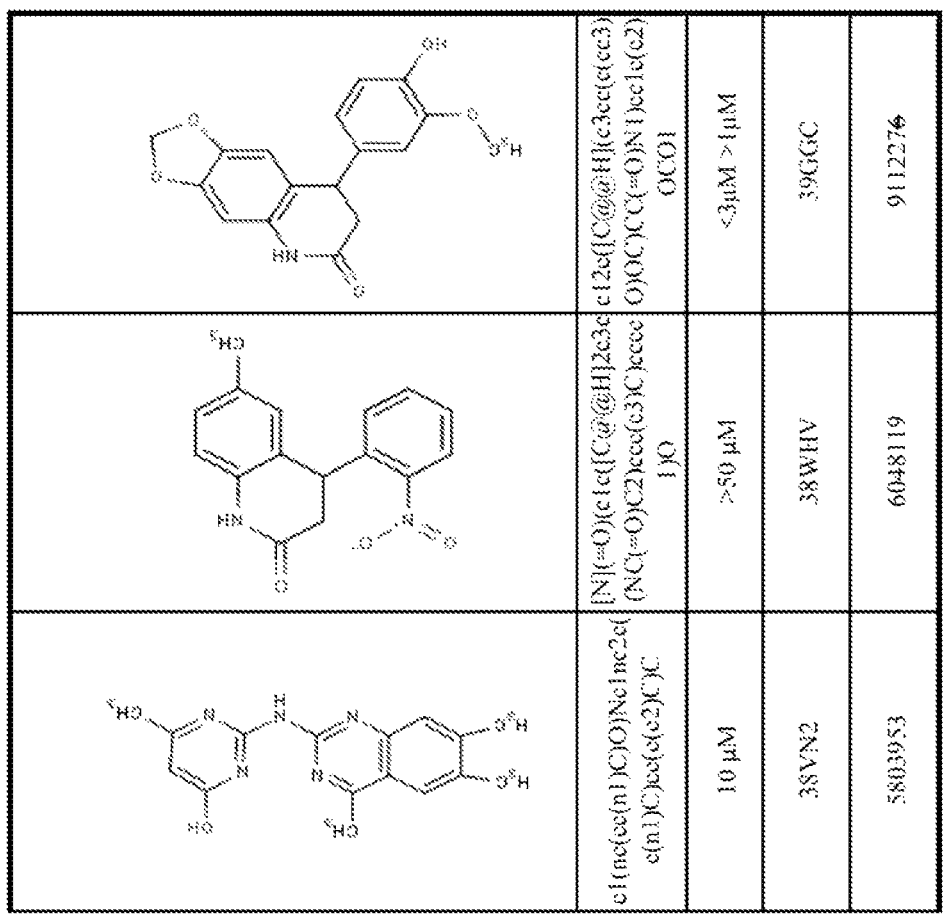

It is well known to those with skill in the chemical and pharmaceutical arts that essentially the same chemical compound may exist in essentially the same chemical form as various tautomers and pharmaceutically acceptable salts. As used herein, the term "tautomer" refers to constitutional isomers of organic compounds that readily interconvert by the formal migration of a hydrogen atom or proton, accompanied by a switch of a single bond and adjacent double bond. The exact ratio of the tautomers depends on several factors, including temperature, solvent, and pH. As used herein, the term "pharmaceutically acceptable salt" refers to an ionizable drug that has been combined with a counter-ion to form a neutral complex. Converting a drug into a salt through this process can increase its chemical stability, render the complex easier to administer, and allow manipulation of the agent's pharmacokinetic profile (Patel, et al., 2009). In particular, the compounds disclosed in FIGS. 1-2 are intended to encompass all tautomers and pharmaceutically acceptable salts.

The term "p53" as used herein also and equivalently may be called P53, TP53, TRP53, TSP53, WRAP53, BCC7, LFS1, tumor protein p53, tumor suppressor p53, tumor suppressor protein p53, phosphoprotein p53, cellular tumor antigen p53, non-viral tumor antigen p53, transformation-related protein p53, transformation-associated protein p53, NCBI GeneID:7157, HGNC:11998, MIM:191170, RefSeq: NP_000537, antigen NY-CO-13, or other names familiar to those skilled in the art.

The human p53 protein sequence as used herein corresponds to GenBank locus X54156, which is also National Center for Biotechnology Information (NCBI) sequence ID NG_017013. The human p53 atomic structural 3-dimensional coordinates of the p53 core domain as used herein correspond to Protein Data Bank (PDB) structure ID 1TSR chain B. The human cell line (Saos-2) used in the biological assays described below corresponds to FIG. 3E in reference (Lambert, et al., 2009).

Related DNA sequences include, but are not limited to, NCBI sequence IDs NM_001276699, NM_001276698, NM_001276697, NM_001276696, NM_001276695, NM_001276761, NM_001276760, NM_001126118, NM_001126114, NM_001126113, NM_001126112, NM_000546.5, NM_001126117.1, NM_001126116.1, NM_001126115, NM_001143991, NM_001143991, and NM_001143990. Related atomic structural 3-dimensional coordinates include, but are not limited to, PDB structure IDs 4MZI, 4IBQ, 4IBS, 4IBT, 4IBY, 4IBZ, 4IJT, 4HFZ, 4KVP, 4LO9, 4LOE, 4LOF, 4BUZ, 4BV2, 3ZME, 4FZ3, 4AGL, 4AGM, 4AGN, 4AGO, 4AGP, 4AGQ, 2YDR, 3TG5, 3Q01, 2YBG, 2XWR, 3PDH, 3OQ5, 3LW1, 2X0U, 2X0V, and 2X0W.

The term "p53 cancer target" as used herein is a protein, cell, cell line, tissue, organ, or organism that is, contains, or expresses a p53 cancer mutant.

The term "p53 cancer mutant" as used herein refers to a mutant version of a p53 protein or polypeptide with reduced tumor suppressor activity.

The term "Cys124" as used herein refers to p53 cysteine residue 124. Cys124 also and equivalently may be called Cys 124, Cys-124, C124, C 124, C-124, or other names familiar to those skilled in the art.

The term "small molecule" as used herein refers to a low molecular weight organic compound that is not a polymer. The upper molecular weight limit for a small molecule is approximately 800 Daltons. The term "compound" or "chemical compound" also may be used to refer to a small molecule.

The term "scaffold" as used herein refers to a generic chemical substructure that is shared by a group of related small molecules; i.e., when such a group of related small molecules each are represented as a molecular graph within which atoms are nodes and chemical bonds are edges, then the term scaffold refers to any such molecular graph that appears as a sub-graph within the molecular graph of each such related small molecule.

The term "scaffold family" of such a scaffold, as used herein, refers to the family of small molecules such that each contains that scaffold in common; i.e., when small molecules each are represented as a molecular graph within which atoms are nodes and chemical bonds are edges, then the term scaffold family refers to the group of small molecules such that the scaffold appears as a sub-graph within the molecular graph of each small molecule that is a member of that scaffold family.

In some embodiments, the phrase "a person in need of such treatment" can refer to an individual who has a cancer, wherein the cancer expresses a mutated version of p53. In some embodiments, the p53 mutant is susceptible to enhanced p53 activity as defined above, wherein the enhancement results from a small molecule or group of related small molecules as disclosed herein.

Drugs known to be used for individuals suffering from p53-based cancers include, but are not limited to, general chemotherapeutics. Examples of general chemotherapeutics include, but are not limited to, Avastin, Rituxan, Herceptin, Taxol, and Gleevec. Experimental drugs include, but are not limited to, PRIMA-1, CP-31398, and CDB3; see (Stoklosa & Gokb, 2005) and other References below.

Therapies used for the treatment of p53 based cancers include, but are not limited to, surgery, chemotherapy, and radiation therapy. Experimental therapies include, but are not limited to, expression of wild-type p53 in tumors based on virus-based delivery vectors.

In some embodiments, a subject can be treated with a pharmaceutical composition containing a compound that enhances p53 activity. A pharmaceutical composition will typically contain a pharmaceutically acceptable carrier. Although oral administration of a compound is the preferred route of administration, other means of administration such as nasal, topical or rectal administration, or by injection or inhalation, are also contemplated. Depending on the intended mode of administration, the pharmaceutical compositions may be in the form of solid, semi-solid, or liquid dosage forms, such as, for example, tablets, suppositories, pills, capsules, powders, liquids, suspensions, ointments, or lotions, preferably in unit dosage form suitable for single administration of a precise dosage. One skilled in this art may further formulate the compound in an appropriate manner, and in accordance with accepted practices, such as those disclosed in Remington's Pharmaceutical Sciences, Gennaro, Ed., Mack Publishing Co., Easton, Pa. 1990.

A carrier can be any and all solvents, dispersion media, vehicles, coatings, diluents, antibacterial and antifungal agents, isotonic and absorption delaying agents, buffers, carrier solutions, suspensions, colloids, and the like. A pharmaceutical carrier can include, but is not limited to, liposomes, albumin microspheres, soluble synthetic polymers, DNA complexes, protein-drug conjugates, carrier erythrocytes, and any other substance that is incorporated to improve the delivery and the effectiveness of drugs. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

A therapeutically effective amount is an amount of a compound effective to prevent, alleviate, or ameliorate symptoms of disease or prolong the survival of the subject being treated. Determination of a therapeutically effective amount is well within the capability of those skilled in the art, especially in light of the detailed disclosure provided herein. The effective dosage, level, or amount of a compound to be used in vivo can be determined by those skilled in the art, taking into account the disorder to be treated, the condition of the individual patient, the site of delivery, the method of administration, the potency, bioavailability, and metabolic characteristics of the compound, and other factors.

Examples of cancers that frequently express mutant forms of p53 include, but are not limited to, lung, breast, colorectal, ovarian, and pancreatic cancers. Mutant forms of p53 may be found in all types of human cancers, with an occurrence frequency that varies depending on the type of cancer.

In various embodiments, compounds that enhance p53 activity are not PRIMA-1, PRIMA-1-MET [APR-246], or MQ [methylene quinuclidinone] (Bykov, et al., 2002; Lambert, et al., 2009); STIMA-1 (Zache, et al., 2008); NB [3-methylene-2-norbornanone] (Reddy, et al., 2004]); MIRA-1, MIRA-2, or MIRA-3 [maleimide analogs] (Bykov, et al., 2005); NSC319725 or NSC319726 (Yu, et al., 2012); CP-31398 (Demma, et al., 2004); SCH529074 (Demma, et al., 2010); PARP-PI3K (Gonzalez-Billalabeitia, et al., 2014); RITA [5,50-(2,5-furandiyl)bis-2-thiophenemethanol] (Issaeva, et al., 2004); MPK-09 (Metri, et al., 2013); Zn-curc [curcumin-based Zn(II)-complex] (Garufi, et al., 2013); P53R3 (Weinmann, et al., 2008); a (2-benzofuranyl)-quinazoline derivative (Sutherland, et al., 2011); a nucleolipid derivative of 5-fluorouridine (of 5-FU or 5-FUrd) (Farhat, et al., 2014); a derivative of 2-aminoacetophenone hydrochloride (Myers, et al., 2005); or PK083 [PhiKan83], PK5174, or PK7088 (Basse, et al., 2010; Boeckler, et al., 2008; Liu, et al., 2013, Wilcken, et al., 2012); all of which are compounds that have been reported previously in the scientific literature to enhance p53 activity in p53 cancer mutants.

The present invention may be better understood by referring to the accompanying examples, which are intended for illustration purposes only and should not in any sense be construed as limiting the scope of the invention.

EXAMPLE 1

2. p53 Cancer Mutant Functional Reactivation Studies

We have studied p53 reactivation for several years (Danziger et al., 2006, 2007, 2009; Bichutskiy, et al., 2007; Baronio et al., 2010; Demir et al., 2011; Wassman et al., 2013). Both second-site suppressor mutations ("rescue mutants") and a small handful of small molecules are able to reactivate p53 through restabilization of the mutant protein.
2.1. Several Small Molecules are Disclosed that are Intended to Enhance p53 Activity in p53 Cancer Mutants.

Using the biological and computational methods described below, stictic acid (Wassman, et al., 2013) and the novel p53 reactivation compounds shown in FIGS. 1-2 were identified. The compounds shown in FIG. 1 were selected by computational ranking of 1,738,752 compounds in the Zinc Leads Now chemical compound library (http://zinc.docking org/subsets/leads-now), version of January, 2011, using the computational methods described below, and validated by assaying 138 compounds using the biological methods described below. The compounds shown in FIG. 2 were identified by computational ranking of 448,532 compounds in the Chembridge Express Pick Library 2012 chemical compound library (http://www.chembridge.com/screening_libraries/index.php#EXPRESS-Pick) using the computational methods described below, and validated by assaying 38 compounds using the biological methods described below.

3. Our Discovery of a Novel p53 Reactivation Drug Binding Site.

We have found that identification of small molecules that enhance p53 activity can be significantly improved using computational methods to rank or prioritize compounds from chemical libraries or virtual synthetic schemes, and thereafter applying the biological methods described below only to the top-ranked compounds. The novel p53 binding site—open binding site L1/S3—that we discovered (Wassman, et al., 2013) makes our computational methods much more effective. The brief description of such methods here is intended to be illustrative, but neither limiting nor exhaustive.
3.1. Initial Identification of a Novel p53 Binding Site by Ensemble-Based Virtual Docking.

A preferred embodiment uses the computational method of virtual docking as the initial step to identify compounds that are predicted to bind strongly to the target protein. In this method, the binding of the compound and the target protein is simulated computationally, and an estimate is made of the goodness of fit. Compounds are ranked according to the estimated goodness of fit for the compound docked to the target protein. Many different methods of virtual docking are known to those skilled in the art.

A practical difficulty to this approach, which is solved in the present invention, is that the p53 compound binding site is "closed" in the reference human p53 crystal structure, PDB ID 1TSR-B (Cho, et al., 1994). Therefore, most standard attempts to employ virtual docking methods fail because the target binding site is not accessible to the compound in the target protein structure.

We have discovered that human p53 can adopt an "open" binding site conformation during molecular dynamics (MD) simulations (Wassman, et al., 2013). This open cavity presents a favorable binding area for small molecules.
3.2. Computational Identification of the Discovered Open Binding Site Around L1/S3.

Figure 4:
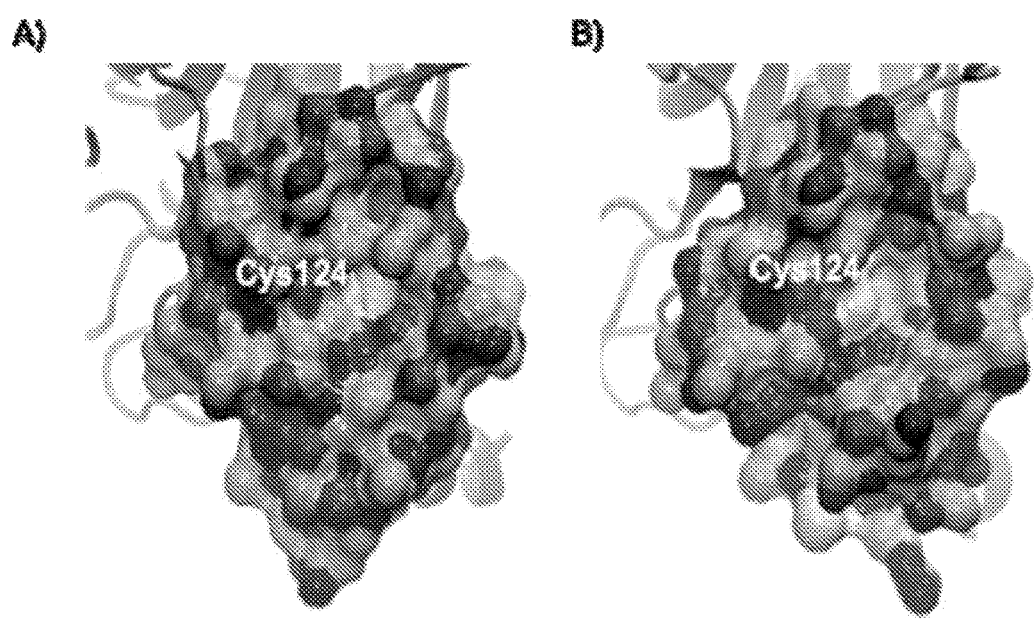
FIG. 4 is a panel showing the structure of 1TSR (Cho, et al., 1994) chain B displaying all p53 residues within 10 Å of Cys124 in a surface representation.

Initial docking calculations suggested preferential binding of MQ, an active degradation product of PRIMA-1 (Lambert, et al., 2009), to a region in the mouse p53 crystal structure (89% sequence identity to human p53; PDB ID 3EXJ; Malecka, et al., 2009). Our genetic experiments had labeled this region as highly enriched for rescue mutations in human p53 (Wassman, et al., 2013). Thus, structural changes in this region could be expected to favor p53 cancer rescue. As well, cysteine residue 124 (C124) was at the center of this putative p53 reactivation region (FIG. 4); covalent attachment of MQ to a cysteine thiol group had been suggested to be essential for p53 reactivation by PRIMA-1 decomposition products (Lambert, et al., 2009); and the computationally predicted MQ binding pose placed the reactive methylene in a favorable orientation for cysteine alkylation of C124 (Wassman, et al., 2013). The region in the human p53 core domain is flanked by loop L1 and sheet S3 (hence, the L1/S3 pocket).

Close inspection of the reference human p53 crystal structure (Cho, et al., 1994) indicated that C124 was somewhat occluded and would be difficult to access for molecules much larger than water (FIG. 4A). This structural occlusion may be ameliorated due to the marginal stability of p53 at physiological temperature, which suggests a high degree of intrinsic flexibility. To explore the flexibility of p53, we investigated human wild type p53, cancer mutant R273H, and cancer rescue mutant R273H_S240R in identical procedures using all-atom explicit solvent molecular dynamics (MD) simulations.
3.2.1. Molecular Dynamics Simulations A preferred embodiment employs explicitly solvated molecular dynamics simulations. Starting structures for simulations are obtained from the Protein Data Bank (PDB; ID: 1TSR, chain B; Cho, et al., 1994) and all crystallographically resolved water molecules are retained. Histidine protonation states are determined by WHATIF web interface. All other missing hydrogen atoms are added according to the AMBER9 topology parameters using the LEAP module within the AMBER9 program. MOLPROBITY is used to detect and correct flipped side-chains of asparagine, glutamine, and histidine residues. The protein is solvated in a rectangular box of TIP3P waters constituting an 8 Å buffer from the protein to the periodic boundary in all directions. Chloride ions are added to neutralize total system charge. Topology files are built using the Amber FF99SB force field. Zinc is modeled using the cationic dummy atom approach. The composite system is about 27,000 atoms total. Wild-type p53 is mutated using the AMBER9 LEAP module of AMBER9 just before solvating the protein in TIP3P waters.

A total of 28,000 steps of energy minimization are carried out to remove artificial contacts. Hydrogen atoms are relaxed in the first 2,000 steps, holding all other atoms fixed. Hydrogen atoms, water, and ions are relaxed in the following 2,000 steps. In the third 2,000 steps, the four residues around $Zn^{+2}$ ions are relaxed as well as hydrogens, water, and ions. In the fourth 2,000 steps, the protein backbone is held fixed, minimizing all other atoms. Finally, all atoms are minimized without any constraints for 20,000 steps. Following minimization, the system is first equilibrated for 1 ns with a 1 fs timestep at 1 atm pressure and a temperature of 310 K. Equilibration consists of a sequence of four MD simulations during which all atoms except hydrogen atoms are constrained with a force constant of 4.0, 3.0, 2.0, and 1.0 kcal/mol. $Å^2$, respectively. Production dynamics are carried out at 1 atm pressure and a temperature of 310 K for 30 ns without any constraints. The Particle Mesh Ewald algorithm is used for long range electrostatics. A non-bonded cutoff of 10 Å is employed. All minimizations and molecular dynamics simulations are carried out using NAMD2.7. Our systems scaled 0.13 days per nanosecond of simulation on 48 processors. Snapshots are recorded every 0.5 ps of the simulation resulting in 60,000 frames.

The propagation of root-mean-square-deviation (RMSD) of alpha carbons with respect to the initial structure shows that the MD simulations are equilibrated and stable. The frames of each 30 ns trajectory are clustered with respect to the residues within 10 Å of C124 with an RMSD cutoff of 1.65 Å using the GROMOS clustering algorithm (Daura, et al., 1998) within GROMACS (Lindahl, et al., 2001; Hess, et al., 2008). This clustering resulted in 28 clusters in the case of wild-type p53 compared to 41 clusters obtained in the case of R273H cancer mutant, which suggests that the mutant system is less rigid than the wild type protein (Wassman, et al., 2013). As previously mentioned, in the crystal structure C124 lies within an occluded region (FIG. 4A). Structures with more solvent-exposed C124 region are observed in individual MD snapshots (FIG. 4B), as well as among the most dominant cluster representative structures of the R273H mutant. These findings substantiate previous NMR experiments that indicated C124 is solvent exposed approximately 5% of the time in normal solution dynamics (Canadillas, et al., 2006).

3.2.2. Trajectory Clustering

To reduce the redundancy in the MD-generated ensemble, structures extracted from these simulations were then clustered according to the residues within 10 Å of C124 and an RMSD cut-off of 1.65 Å using the GROMOS clustering algorithm. Structures with more solvent-exposed L1/S3 region were observed in individual MD snapshots as well as among cluster representative structures of all simulated proteins. According to the calculations of binding pocket volume around C124 using the FPocket program (Le Guilloux, et al., 2009), a large "druggable binding pocket" is observed around C124 for approximately 7.3% of 3000 frames of the cancer mutant R273H trajectory (FIG. 4B). These findings are consistent with previous NMR experiments that indicate C124 is solvent exposed approximately 5% of the time in normal solution dynamics (Canadillas, et al., 2006).

3.2.3. In Silico Docking

We next performed in silico docking studies to evaluate favorable binding sites on the surface of p53 and assess docking of small molecules near C124. As a positive control system for docking, we used the 2VUK PDB structure and redocked its crystallized bound p53 cancer rescue ligand PhiKan083 (Boeckler, et al., 2008). AutoDock Vina (Trott & Olson, 2010) replicated the crystal binding pose of PhiKan083 to within 1 Å RMSD (computed over all heavy atoms). Subsequent blind docking of active ligands (namely Mira-1 [Bykov, et al., 2005], PRIMA-1 [Lambert, et al., 2009], MQ [Lambert, et al., 2009], Stima-1 [Zache, et al., 2008], and 3-methylene-2-norbornanone [NB; Reddy, et al., 2004]) to the 1TSR-B crystal structure (Cho, et al., 1994) revealed that none of the compounds bound favorably in the vicinity of C124, nor to any other cysteine residues in the reference human p53 crystal structure 1TSR-B, because that structure does not reveal an open binding pocket.

Ensemble-based docking is emerging as a new paradigm in virtual screening and drug discovery, especially in the case of highly flexible receptors (Amaro, et al., 2008; Amaro & Li, 2010; Durrant, et al., 2010). We generated and clustered p53 conformations as described in Section 3.2.2. By visual inspection and pocket volume calculations, representative frames of cluster 11 and cluster 13 were chosen as the most solvent-exposed in the L1/S3 region for the wild-type and the R273H cancer mutant, respectively. Blind docking to the cluster 13 representative frame of the R273H cancer mutant identified C124 as the only cysteine residue that presents a favorable binding site within 4 Å of the compounds. Similarly, blind docking to the cluster 11 representative frame of the wild type indicated that the active compounds dock in close vicinity of C124, but not close to any other cysteines. These results suggest that L1/S3 may present an area favorable to ligand binding during its normal solution dynamics, despite the lack of this area in the human p53 crystal structure 1TSR-B (Cho, et al., 1994).

3.2.4. Computational Characterization of the L1/S3 "Open" Binding Site.

We analyzed the "open" structures extracted from the MD-generated ensemble (described in section 3.2.3) to characterize the criteria that distinguish open from closed Cys124 binding site conformations. In this section, (1) first the criteria are listed; (2) then the p53 wild-type and R273H mutant MD ensembles are analyzed, and (3) finally, other slightly open or solvent-accessible PDB crystal structures of p53 are discussed. The conclusion of this analysis is that at the time of writing there did not exist an "open" structure in any currently available natural PDB crystal structure of p53 that is as open as we found in structures extracted from the MD simulations (section 3.2.3). The Cys124 "open" conformation is our novel discovery (Wassman, et al., 2013).

3.2.4.1. Criteria that Distinguish L1/S3 "Open" from "Closed" Binding Sites.

The criteria consist of an amino acid composition criterion and a distance geometry criterion based upon the human p53 sequence as described above (GenBank locus X54156, also NCBI sequence ID NG_017013; Protein Data Bank (PDB) structure ID 1TSR chain B).

The amino acid composition criterion is that the binding site is lined by residues Val122, Thr123, Pro142, Leu114, Ser121, Cys124, Thr231, Cys141, Ser116, Gln144, and Phe113.

The distance geometry criterion consists of five constraints, as expressed in Table 1. The five constraints, as stated in words, are that:
1. Either the distance between Pro142's beta carbon and Leu114's delta carbon 1 atom (Leu114.CD1) or the distance between Pro142's beta carbon and Leu114's delta carbon 2 atom (Leu114.CD2) should be greater than 5.6 A.
2. Both the distance between Pro142's beta carbon and Leu114's delta carbon 1 atom (Leu114.CD1) and the distance between Pro142's beta carbon and Leu114's delta carbon 2 atom (Leu114.CD2) should be greater than 4.9 A.
3. Either the distance between Cys124's alpha carbon and Leu114's delta carbon 1 atom (Leu114.CD1) or the distance between Cys124's alpha carbon and Leu114's delta carbon 2 atom (Leu114.CD2) should be greater than 10.8 A.
4. Both the distance between Cys124's alpha carbon and Leu114's delta carbon 1 atom (Leu114.CD1) and the distance between Cys124's alpha carbon and Leu114's delta carbon 2 atom (Leu114.CD2) should be greater than 9.0 A.
5. The dihedral angle of Leu114's N atom, Leu114's alpha C, Leu114's beta C atom, and Leu114's gamma C atom should either be less than 40 degrees, or larger than 80 degrees.

TABLE 1

| Geometric Constraints | Requirements |
| --- | --- |
| (Pro142.CB-Leu114.CD2 > 5.6 A), (Pro142.CB-Leu114.CD1 > 5.6 A) | At least one true |
| (Pro142.CB-Leu114.CD2 > 4.9 A), (Pro142.CB-Leu114.CD1 > 4.9 A) | Both true |
| (Cys124.CA-Leu114.CD2 > 10.8 A), (Cys124.CA-Leu114.CD1 > 10.8 A) | At least one true |
| (Cys124.CA-Leu114.CD2 > 9.0 A), (Cys124.CA-Leu114.CD1 > 9.0 A) | Both true |
| (Dihedral angle (Leu114.N-Leu114.CA-Leu114.CB-Leu114.CG) > 80°), (Dihedral angle (Leu114.N-Leu114.CA-Leu114.CB-Leu114.CG) < 40°) | At least one true |

The same five distance geometry constraints, as expressed in Table 1 and stated here in an equivalent mathematical expression, are that:
((Pro142.CB-Leu114.CD2>5.6 A) or (Pro142.CB-Leu114.CD1>5.6 A)) and
((Pro142.CB-Leu114.CD2>4.9 A) and (Pro142.CB-Leu114.CD1>4.9 A)) and
((Cys124.CA-Leu114.CD2>10.8 A) or (Cys124.CA-Leu114.CD1>10.8 A)) and
((Cys124.CA-Leu114.CD2>9.0 A) and (Cys124.CA-Leu114.CD1>9.0 A)) and
((dihedral angle (Leu114.N-Leu114.CA-Leu114.CB-Leu114.CG)>80 degrees) or
(dihedral angle (Leu114.N-Leu114.CA-Leu114.CB-Leu114.CG)<40 degrees)).

3.2.4.2. Criteria as Applied to the p53 Wild-Type and R273H Mutant MD Ensembles.

Using the criteria of section 3.2.4.1, 6.3% of the frames in the p53 wild-type MD ensemble are open. Using those criteria, however, the PDB p53 wild-type structures in PDB ID 1TSR are closed. These criteria indicate that 5.0% of the frames in the R273H MD ensemble are open. The R273H cluster 13 representative (section 3.2.3) is open with these criteria.

3.2.4.3. Other Slightly Open or Solvent-Accessible PDB Crystal Structures of p53.

The p53 structure in PDB ID 3IGL is solvent-accessible around Cys124, but still the pocket is closed using the criteria provided in section 3.2.4.1:
Pro142.CB-Leu114.CD2=5.69 A,
Pro142.CB-Leu114.CD1=4.11 A,
Cys124.CA-Leu114.CD2=10.68 A (two cysteine conformers in X-ray structure), Cys124.CA-Leu114.CD1=8.78 A (two cysteine conformers in X-ray structure),
dihedral angle (Leu114.N-Leu114.CA-Leu114.CB-Leu114.CG)=−67.84 degrees.

The p53 structure in PDB ID 3D06 is solvent-accessible around Cys124 but is missing residues 115-121 (the protein segment following the critical Leu114). Thus, the entire binding pocket conformation is not known, and so the structure is poorly suited as a basis for computational drug discovery. Whether the structure is open or closed cannot be determined with certainty because critical parts of the structure are missing.
Pro142.CB-Leu114.CD2=3.71 A,
Pro142.CB-Leu114.CD1=5.85 A,
Cys124.CA-Leu114.CD2=9.32 A (two cysteine conformers in X-ray),
Cys124.CA-Leu114.CD1=10.26 A (two cysteine conformers in X-ray),
dihedral angle (Leu114.N-Leu114.CA-Leu114.CB-Leu114.CG)=−82.72 degrees.

The p53 structure in PDB ID 3D05 is solvent-accessible around Cys124 but is missing residues 115-121 (the protein segment following the critical Leu114). Thus, the entire binding pocket conformation is not known, and so the structure is poorly suited as a basis for computational drug discovery. Whether the structure is open or closed cannot be determined with certainty because critical parts of the structure are missing.
Pro142.CB-Leu114.CD2=5.79 A,
Pro142.CB-Leu114.CD1=4.27 A,
Cys124.CA-Leu114.CD2=10.46 A,
Cys124.CA-Leu114.CD1=8.62 A,
dihedral angle (Leu114.N-Leu114.CA-Leu114.CB-Leu114.CG)=−72.08 degrees.

The p53 structure in PDB ID 2BIQ is solvent-accessible around Cys124 but is missing residues 115-121 (the protein segment following the critical Leu114). Thus, the entire binding pocket conformation is not known, and so the structure is poorly suited as a basis for computational drug discovery. Whether the structure is open or closed cannot be determined with certainty because critical parts of the structure are missing.
Pro142.CB-Leu114.CD2=5.54 A,
Pro142.CB-Leu114.CD1=4.11 A,
Cys124.CA-Leu114.CD2=10.73 A,
Cys124.CA-Leu114.CD1=9.51 A,
dihedral angle (Leu114.N-Leu114.CA-Leu114.CB-Leu114.CG)=−75.87 degrees.

The p53 structure in PDB ID 2J21 is solvent-accessible around Cys124 but is missing residues 116-121 (the protein segment following the critical Leu114 after one residue). Thus, the entire binding pocket conformation is not known, and so the structure is poorly suited as a basis for computational drug discovery. Whether the structure is open or closed cannot be determined with certainty because critical parts of the structure are missing.

Pro142.CB-Leu114.CD2=5.77 A (5.70 A in chain B),
Pro142.CB-Leu114.CD1=4.19 A (4.07 A in chain B),
Cys124.CA-Leu114.CD2=10.99 A (10.63 A in chain B),
Cys124.CA-Leu114.CD1=9.34 A (8.66 A in chain B),
dihedral angle(Leu114.N-Leu114.CA-Leu114.CB-Leu114.CG)=−65.14 degrees (−65.45 degrees in chain B)

The 35 p53 structures in PDB ID 2FEJ are solution structures determined using isotopic labeling techniques and NMR spectroscopy. None of these 35 structures 2FEJ.pdb exhibit open Cys124 pockets using the criteria of section 3.2.4.1. Several are solvent-accessible in the area of Cys124 but are occluded in that area. The last frame values, and the ranges (in parentheses), are given below for these criteria.

Pro142.CB-Leu114.CD2=5.12 A, (6.75>x>3.00 A)
Pro142.CB-Leu114.CD1=3.31 A, (7.25>x>3.00 A)
Cys124.CA-Leu114.CD2=9.62 A, (9.50>x>4.25 A)
Cys124.CA-Leu114.CD1=8.46 A, (8.75>x>3.75 A)
dihedral angle (Leu114.N-Leu114.CA-Leu114.CB-Leu114.CG)=−91.25 degrees. (70>x>−130 degrees).

The p53 structure in PDB ID 3EXJ, from mouse, is closed using these criteria:

Pro139.CB-Leu111.CD2=4.66 A,
Pro139.CB-Leu111.CD1=6.60 A,
Cys121.CA-Leu111.CD2=6.90 A,
Cys121.CA-Leu111.CD1=6.66 A,
dihedral angle (Leu111.N-Leu111.CA-Leu111.CB-Leu111.CG)=52.43 degrees.

3.3. Biological Validation of the Binding Site Hypothesis.

Although the region around residue C124 is enriched for cancer rescue mutations, changes in position 124 have never been found, nor were they predicted by our SVM classifier, to reactivate p53 cancer mutants. Indeed, directed saturation mutagenesis of position 124 in the context of the R175H p53 cancer mutation explored all single amino acid changes at C124 and confirmed the absence of any genetic mutation rescue activity at this position. We could therefore test the computer predictions for a role of C124 in covalent drug binding in vivo by changing C124 into alanine to prevent the hypothetical thiol-mediated link with MQ.

Figure 5:
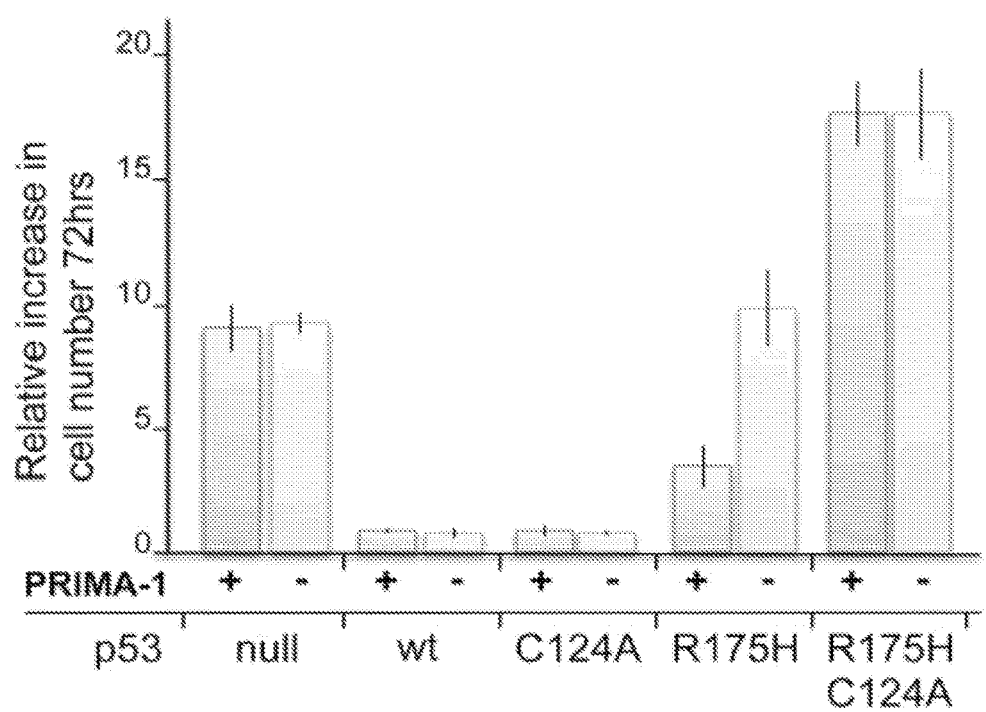
FIG. 5 is a graph showing that PRIMA-1 acts through cysteine 124 in p53. p53null Saos-2 cells expressing wild type p53, or the indicated p53 mutants, were treated with 50 μM pre-heated PRIMA-1 ("+", left bar) or the medium without PRIMA-1 (DMSO, "−", right bar) for 72 h. The increase in cell number during 72 h of growth is shown. Standard deviations represent 4 independent samples (Wassman, et al., 2013).

Consistent with our previous results, changing C124 into A124 had little effect on otherwise wild-type p53 and did not reactivate the R175H p53 cancer mutant, as determined by activity assays in human cells. As expected, addition of PRIMA-1 to cells expressing the inactive R175H p53 led to reactivation and induction of cell death, as seen in FIG. 5. Remarkably, introduction of A124 in R175H-p53 completely eliminated the PRIMA-1 effects. These results provided strong experimental support for the computational prediction of L1/S3 as a major covalent attachment site for PRIMA-1 metabolites (i.e., MQ) and the importance of this region for p53 cancer mutant reactivation.

FIG. 5 shows that PRIMA-1 acts through cysteine 124 in p53 (Wassman, et al., 2013). p53null Saos-2 cells expressing wild type p53, or the indicated p53 mutants, were treated with 50 μM pre-heated PRIMA-1 ("+", left bar) or the medium without PRIMA-1 (DMSO, "−", right bar) for 72 h. The increase in cell number during 72 h of growth is shown. As expected, the p53 cancer mutant R175H was activated by PRIMA-1. Mutating cysteine 124 to alanine blocked PRIMA-1 induced cancer mutant reactivation.

4. Computational Prediction and Biological Validation of p53 Rescue Compounds

Initially, we selected 45 compounds that were predicted by our computational tools to enhance p53 activity in p53 cancer mutants, out of 2,298 possible compounds considered from the National Cancer Institute (NCI) Defined Therapeutics Program (DTP, http://dtp.cancer.gov/repositories.html). When screened against our biological assays (section 4.3 below), one of those 45 compounds, stictic acid, proved to be a p53 reactivation compound as described in (Wassman et al., 2013).

Encouraged, we used our computational tools together with our "open" L1/S3 pocket (Wassman et al., 2013; section 3 above) to identify 138 small molecules that were predicted to enhance p53 activity in p53 cancer mutants, out of 1,738,752 possible compounds considered from the ZINC Leads Now chemical database, version of January, 2011 (http://zinc.docking.org/subsets/leads-now). Sixteen active compounds resulted after biological assay (section 4.3 below), which are shown in FIG. 1 and described in section 4.1 below.

Further encouraged, we used our computational tools together with our "open" L1/S3 pocket (Wassman et al., 2013; section 3 above) to identify 38 small molecules that were predicted to enhance p53 activity in p53 cancer mutants, out of 448,532 possible compounds that were considered from the Chembridge Express Pick Library 2012 chemical database (http://www.chembridge.com/screening_libraries/index.php#EXPRESS-Pick). Eight active compounds resulted after biological assay (section 4.3 below), which are shown in FIG. 2 and described in section 4.2 below.

4.1. Sixteen Active Compounds Selected From Zinc Leads Now.

In summary:

(1) We performed a virtual screen of the ZINC Leads Now chemical database, containing 1,738,752 compounds (version of January, 2011), and computationally extracted 9,668 compounds, designated Set A, that met the criteria described in section 4.1.1.

(2) Our computational tools selected 138 compounds representing diverse scaffolds and properties as a library for biological assays, designated Set B, as described in section 4.1.2:

(2.a) 46 non-enone compounds that had top ranked combined docking scores, diverse scaffolds, and were available for purchase;

(2.b) 46 enone compounds that had top ranked combined docking scores, diverse scaffolds, and were available for purchase; and (2.c) 46 compounds, chosen from the 17,387 compounds in the top one percent of ZINC Leads Now by favorable docking scores, that were available for purchase and not selected in either of the two groups above.

Figure 3:
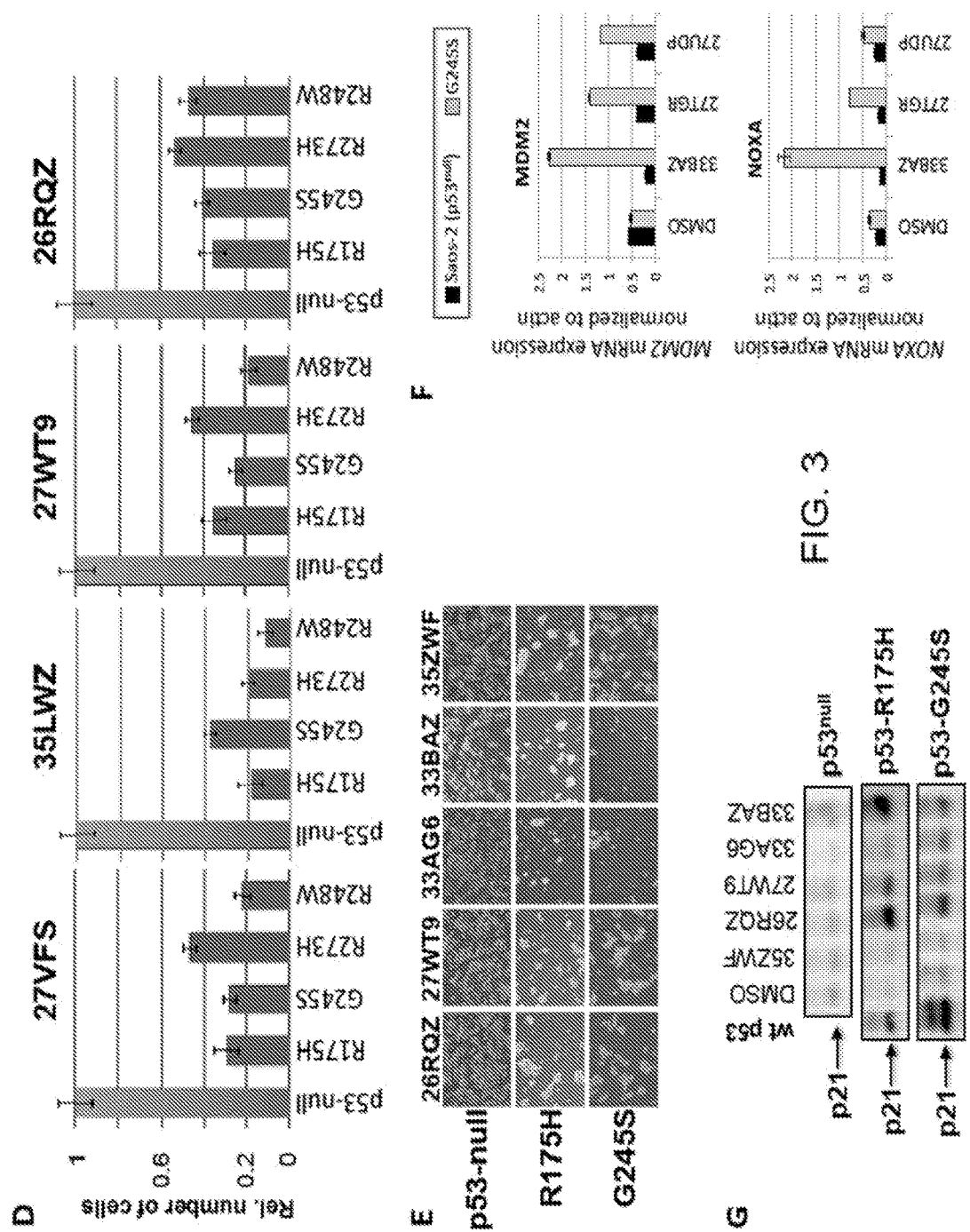
FIG. 3 is a panel of biological data for the 24 compounds described herein, which are shown in FIGS. 1-2 and described below in section 4.

(3) Our biological assays identified sixteen of those 138 compounds as p53 reactivation compounds, as described in section 4.3 and shown in FIGS. 1 & 3.

4.1.1. Set A: 9,668 Candidate Compounds Selected from Zinc Leads Now.

We performed a virtual screen of the ZINC Leads Now chemical database, containing 1,738,752 compounds (version of January, 2011). It was necessary to modify our usual screening procedure in order to accommodate the computational demands of such a large virtual screening effort. Instead of performing an initial ensemble-weighted virtual screen (Relaxed Complex Scheme) using the most-populated 15 cluster representatives as in the case of previous smaller databases, we performed a virtual screen using only the cluster 13 "open" p53_R273H representative frame (Wassman, et al., 2013). This modification reduced the computational time 15-fold (30-fold if compared to the ensemble-based virtual screening with the top 30 cluster centroids). As a control, we showed that this modified method increased efficiency with little or no loss of information. The top-ranked 17,387 compounds (one percent of the ZINC Leads Now database) were filtered for ADME properties (Rule of 5, Rule of 3, and log Poct/wat≤3) and the resulting 9,668 compounds were chosen for further datamining. These 9,668 compounds are designated as Set A.

4.1.2. Set B: Selection of 138 Zinc Leads Now Compounds for Assay.

Our computational tools selected 138 compounds representing diverse scaffolds and properties as a pilot library for biological assays. These 138 compounds are designated as Set B. They were selected as follows:

The compounds of Set A were docked against the same mutant conformation (R273H) as described above except using the Surflex docking software (Jain, et al., 2003, 2007). The docking scores from Autodock Vina and Surflex were normalized and a combined (mean) normalized score was calculated for each compound.

All compounds of Set A were used to produce one or more chemical scaffolds by the Leadscope Personal software (http://www.leadscope.com/). Each such scaffold describes a related group of small molecules containing the common chemical sub-structure described by their common scaffold.

A handful of compounds with an enone group have been reported in the recent p53 literature (Lambert, et al., 2009). The enone group can react with cysteine side-chains. The compounds in Set A with an enone group were extracted by visual inspection of their chemical structure.

The combined docking scores of compounds, the structural diversity obtained from scaffold classification of compounds, and the availability of compounds for purchase were considered for compound selection.

A total of 138 compounds were selected from the 9,668 compounds of Set A according to the three groups described below:

46 non-enone compounds, chosen from Set A, that had top ranked combined docking scores, diverse scaffolds, and were available for purchase;

46 enone compounds, chosen from Set A, that had top ranked combined docking scores, diverse scaffolds, and were available for purchase; and 46 compounds, chosen from the 17,387 compounds in the top one percent of ZINC Leads Now by favorable docking scores with Autodock Vina (Trott & Olson, 2010), that were available for purchase and not selected in either of the two groups above. Of these 46 compounds, 32 appeared in Set A and 14 did not appear in Set A.

These 138 (=3×46) compounds are designated as Set B.

4.1.3. Biological Assay Result of Set B.

The sixteen active compounds that resulted from Set B after assay (section 4.3 below) are shown in FIG. 1. The corresponding biological assay results are shown in FIG. 3.

4.2. Eight Active Compounds Selected From the Chembridge Library.

In summary:

(1) We filtered the Chembridge Express-Pick Library chemical database, containing 448,532 compounds (version of January, 2011), for cheminformatic properties, then performed a virtual screen of the surviving candidates, and computationally extracted 2,051 compounds that met the criteria described in section 4.2.1.

(2) We used our computational methods to select from those 2,051 compounds and the Chembridge library a set of 456 purchased and physically obtained compounds, designated Set C, as described in section 4.2.2.

(3) We used our machine learning methods (based on Set B, above) to initialize Set D with 81 compounds from Set C that were predicted to be active by our classifiers, as described in section 4.2.3.1.

(4) We added to Set D the 58 compounds from Set C that had docking scores better than −7.1 and were not already in Set D, as described in section 4.2.3.2.

(5) Human chemists with expertise in pharmaceutical drug discovery and chemical synthesis examined Set D and discarded 33 candidates likely to be hydrolyzable, Michaels acceptors (covalent binders), non-drug-like, or otherwise unlikely to have good properties as drug leads, as described in section 4.2.3.3.

(6) We performed MD simulations on the remaining candidates and discarded from Set D the 73 compounds that scored higher than 25 on our Number-Of-Clusters (NOC) (Demir, et al., 2011) metric. We retained in Set D the 33 candidates that scored 25 or lower on our NOC metric, as described in section 4.2.3.4.

(7) We performed a substructure query in Canvas (Schrodinger package, above) across the 456 compounds in Set C in order to identify compounds that are similar to 39CME (FIGS. 1 & 3). The query returned six similar compounds, one of which was already in Set D. The other five compounds were added to Set D, for a total of 38 compounds in Set D.

(8) Our biological assays identified eight of those 38 compounds as p53 reactivation compounds, as described in section 4.3 and shown in FIGS. 2-3.

4.2.1. Initial Library Filtering.

The Chembridge Express Pick Library 2012 contained 448,532 compounds. We first filtered those 448,532 compounds based on cheminformatic properties, resulting in 101,692 filtered compounds (section 4.2.1.1). Then we filtered those 101,692 candidates based on docking to our "open" L1/S3 binding site, resulting in 2,051 compounds (section 4.2.1.2).

4.2.1.1. Filtering Based on Cheminformatic Properties.

We used the OpenEye Filter protocol (OEChem, version 1.7.7, OpenEye Scientific Software, Inc., Santa Fe, NM, USA, http://www.eyesopen.com, 2010), to remove undesirable compounds, reactive compounds, unwanted functional groups, and unwanted protecting groups. Most of the OpenEye Filter default settings were used. We used the following exceptions to the OpenEye Filter default settings:

Required 250<molecular weight <460;
Removed salts;
Removed duplicate structures;
Removed known aggregators, but "OE predicted aggregators" were left in;
Removed solubility prediction cut-off "poorly" or worse;
Removed <10 rotatable bonds;
Removed compounds with 3 or more (out of 5) Lipinski violations.

The resulting filtered compound set contained 101,692 filtered compounds.

4.2.1.2. Filtering Based on Docking to Our "Open" L1/S3 Binding Site.

We then used our "open" p53_R273H conformation (Wassman, et al., 2013) and the virtual docking program Autodock Vina (Trott & Olson, 2010) to select a set of filtered Chembridge compounds predicted to bind well to the "open" L1/S3 binding site. Out of those 101,692 filtered compounds, only 2,051 compounds had better than −6.5 kcal/mol predicted binding affinity. Those 2,051 compounds were retained for further computational data mining.

4.2.2. Set C: 456 Compounds Selected and Purchased from Chembridge.

We used our computational methods as described below to select from those 2,051 compounds and the Chembridge library a set of 456 purchased and physically obtained compounds. These 456 purchased and physically obtained compounds, which were selected as described below, are designated as Set C.

4.2.2.1. Compounds with Better than −7.1 Kcal/Mol Predicted Binding Affinity.

Out of the 2,051 filtered compounds in section 4.2.1.2, only 99 database entries scored better than −7.1 kcal/mol predicted binding affinity in docking Those 99 database entries corresponded to 80 unique compounds (due to different chemical variants of the same compound, e.g., tautomers, different protonation states, etc.). Those 80 unique compounds were used to initialize Set C.

4.2.2.2. Cluster Centroids with Better than −6.5 Kcal/Mol Predicted Binding Affinity.

Out of the 2,051 filtered compounds in section 4.2.1, 99 candidates already were removed in section 4.2.2.1 above, and 1,952 candidates remained. The 1,952 remaining candidates were clustered using K-means clustering (asking for 300 clusters) based on dendritic binary fingerprints in Schrodinger's Canvas platform (Suite 2012: Canvas, version 1.5, 2012, Schrodinger, LLC, New York, N.Y.). We obtained 288 unique cluster centroid compounds by this method. These 288 cluster centroid compounds also were selected into Set C.

4.2.2.3. Compounds Similar to Stictic Acid (Wassman, et al., 2013).

The OpenEye Filter ROCS module (http://www.eyesopen.com/, above) was used to search the 101,692 filtered compounds of section 4.1.3.1 for compounds with similarity to stictic acid (Wassman, et al., 2013) based on the spatial pattern of shape and polar regions (steric bulk and surface properties). We used a TanimotoCombo similarity score greater than 1.0 and selected into Set C the 20 most similar compounds from each of five runs, where one run was done for each of the five parts of the Chembridge Express-Pick library. A total of 100 compounds (=20 compounds/run×5 runs) was selected into Set C in this way.

4.2.2.4. Further Selection of Set C.

From sections 4.2.2.1-3, we selected 80+288+100=468 candidates in total into Set C. Of those 468 candidates, 460 compounds were unique in the concatenated list and did not repeat the compounds tested/ordered before this step.

Among these 460 unique and non-repetitive compounds, 70 compounds (12 compounds from section 4.2.2.1, 45 compounds from section 4.2.2.2, and 15 compounds from section 4.2.2.3, with 2 common compounds coming from separate lines of selection) were confirmed by Chembridge to be unavailable.

We selected 32 new compounds from section 4.2.2.2 using similar cluster members (if available) to replace the unavailable cluster centroids, and 50 new compounds from section 4.2.2.3 using the ROCS module ranking to replace the unavailable 15 compounds in this set. This updated set of 472 compounds was ordered from Chembridge.

4.2.2.5. Final Selection of 456 Compounds in Set C.

After the final order of 472 compounds above, we actually physically received 456 compounds from Chembridge. The sixteen compounds not received were discarded from Set C. The 456 compounds that were received became the final Set C.

4.2.3. Set D: 38 Compounds from Set C for Biological Assay.

4.2.3.1. Computational Refinement of Set C Based on Data Mining of Set B.

In order to refine Set C further, we applied our computational machine learning methods (Danziger, et al., 2006, 2007, 2009) by exploiting the active compounds of Set B (FIG. 1). We first removed from the active compounds of Set B six putative covalent binders (enones or Michaels acceptors; Lambert, et al., 2009), in order to bias the final selected molecules toward non-covalent binders. The positive set (active set) consisted of the remaining non-covalent binding active compounds. We constructed two disjoint negative sets (control sets). One negative control set consisted of the inactive compounds from Set B. The other negative control set consisted of 100 compounds chosen randomly from the ZINC Leads Now chemical database described above.

For each compound in the positive and negative sets above, we constructed a feature vector consisting of: (a) 881 binary molecular features of the PubChem chemical fingerprint (Wang, et al., 2009); (b) four cross-docking scores from Autodock Vina (Trott & Olson, 2010) and Surflex (Jain, 2003, 2007), where each docked pose from both methods was also scored by the other method too; (c) 36 Tanimoto and Tversky distances (Horvath, Marcou, & Varnek, 2013) from the Pubchem fingerprint of each compound to the PubChem fingerprint of each compound in the active set (during cross-validation, distances to the held-out compound were deleted). The PubChem fingerprints expose compound structure, the docking scores reflect binding, and the Tanimoto/Tversky distances incorporate feedback from experimental results by indicating compound similarity to known active hits.

Conditional Mutual Information (Fleuret, 2004) was used to select features. A Support Vector Machine (Witten & Frank, 2005) was the learning algorithm (Danziger, et al., 2006, 2007, 2009). The result was a computational machine learning classifier system, based on the active non-covalent binders from Set B, which (1) accepts as input a compound of unknown p53 enhancing activity; and (2) produces as output a prediction of whether or not that compound will enhance p53 activity. Cross-validated tests of these classifier systems indicated high accuracy, high enrichment factor, high positive predictive value, and very low False Positive rates, which make these classifiers ideal as screening filters. On the other hand, in cross-validated tests about ⅓ of active compounds considered by these classifiers were falsely predicted to be inactive. These properties make the classifiers ideal filters in a drug discovery setting, but a negative prediction does not necessarily mean that the compound in question is inactive—it simply means that the classifiers are conservative filters that tend to select compounds that are likely to be active, even though at the cost of missing some other active compounds.

We applied these computational classifiers to the 456 compounds in Set C, resulting in 81 compounds that were predicted to be active by the classifiers. Those 81 compounds were selected into Set D.

4.2.3.2. Compounds with Better than −7.1 Kcal/Mol Predicted Binding Affinity.

We added into Set D any compound that scored better than −7.1 kcal/mol predicted binding affinity in the docking runs of section 4.2.2.1 and was not already present in Set D. This step added 58 candidates, for a total of 139 candidates in Set D.

4.2.3.3. Human Visual Inspection.

These 139 candidates were inspected visually by a human computational chemist with expertise in pharmaceutical drug discovery, and by a human organic chemist with expertise in chemical synthesis. Based on their experience, they discarded 33 candidates as likely to be hydrolyzable, Michaels acceptors (covalent binders), non-drug-like, or otherwise unlikely to have good properties as drug leads. This step resulted in 106 compounds remaining in Set D.

4.2.3.4. Computational Refinement of Set D Based on MD/Number-of-Clusters.

In order to refine Set D further, we applied our computational molecular dynamics (MD) methods based on the Number-Of-Clusters (NOC) metric, which we developed previously (Demir, et al., 2011). Number-of-Clusters (NOC) in Molecular Dynamics (MD) simulations discriminated functional activity of p53 cancer and rescue mutants in cell-based assays with approximately 90% accuracy (Demir, et al., 2011). We have extended the original NOC method (Demir, et al., 2011) to discriminate also the functional activity of potential p53 cancer rescue compounds in cell-based assays.

We ran MD simulations (Demir, et al., 2011) of various p53 cancer and cancer-rescue mutants for 30 ns and clustered each trajectory with the GROMOS clustering algorithm (Daura, et al., 1999). This allowed us to describe quantitatively the effect of oncogenic and rescue mutations on the overall dynamics of p53 without focusing on local structural details (Demir, et al., 2011). We employed the number of clusters obtained at a certain RMSD cutoff as a metric of instability. The NOCs exhibited by the cancer mutants were significantly higher than p53 wt, indicating a higher overall degree of instability. The number of clusters (NOC) correlated exceptionally well with mutant thermodynamic stability and mutant functional activity in biological assays (Demir, et al., 2011).

As this single NOC metric successfully discriminated functional (genetically reactivated) from non-functional (inactive) p53 mutants, we tested its use in mutant/drug systems. First, the compound is docked to the "open" L1/S3 pocket of the mutant as described above (section 4.2.1.1). Then the mutant/drug complex is simulated using MD and the Number-Of-Clusters metric is calculated as described in reference (Demir, et al., 2011).

MD runs showed that both stictic acid (Wassman, et al., 2013) and MQ [an active degradation product of PRIMA-1 (Lambert, et al., 2009)] greatly reduced the conformational flexibility of cancer mutant R175H and led to a corresponding decrease in the NOC metric. Additional calibration tests were equally encouraging. The results suggested that we could use the NOC metric to recognize both: (a) protein thermal stabilization upon initial compound binding; and (b) improved induced fit after initial binding.

4.2.3.4.1. Compounds Scoring 25 or Less by the NOC Metric.

The 106 candidates remaining in Set D were simulated using MD and the Number-Of-Clusters (NOC) metric for each was calculated as above. This step resulted in 33 candidates that achieved a score of 25 or less by the NOC metric. The 73 candidates that scored above 25 were discarded from Set D. The 33 candidates that scored 25 or less were retained in Set D.

4.2.3.5. Compounds Similar to 39CME.

A substructure query was performed in Canvas (Schrodinger package, above) across the 456 compounds in Set C in order to identify compounds that are similar to 39CME (FIGS. 1 & 3). The query returned six similar compounds. One of those compounds was already in Set D. The other five similar compounds were added to Set D, for a total of 38 compounds in Set D.

4.2.4. Biological Assay Result of Set D.

The eight active compounds that resulted from Set D after assay (section 4.3 below) are shown in FIG. 2. The corresponding biological assay results are shown in FIG. 3.

4.3. Biological Validation of New p53 Rescue Compounds in Human Cells.

Assays of the Set B and Set D compounds for the R175H cancer mutant are complete, and assays for some other p53 cancer mutants also have been done (FIG. 3). Sixteen of the Set B compounds proved to be p53 reactivation compounds (FIGS. 1, 3A). Eight of the Set D compounds proved to be p53 reactivation compounds (FIGS. 2, 3B).

4.3.1. p53 Reactivation Assays.

Our previous p53 reactivation assays focused on p53-driven expression of the canonical p53 target genes p21 and PUMA (Wassman et al., 2013). However, there is significant evidence that neither p21 nor PUMA expression predict p53 anti-tumor activity (Hock & Vousden, 2012; Li et al., 2012; Valente et al., 2013). Indeed, our results comparing effects of PRIMA-1 and stictic acid support this view. Stictic acid is significantly better than PRIMA-1 in restoring p21 and PUMA expression in p53 cancer mutants, yet PRIMA-1 is considerably more potent in p53-dependent killing/arresting of these cells (Wassman et al., 2013) (compare stictic acid and PRIMA-1 in FIG. 3A). We now use p21 and PUMA expression as an independent transcription assay for p53 cancer mutant reactivation, but not the primary selection criterion. We changed to p53-dependent cell killing (or proliferation arrest) as our main measure of efficacy because our long-term goal is anti-tumor drugs.

The basis for our primary assay is that cancer cells cannot tolerate active p53, stop proliferation, and eventually die. Expression of functional p53 in p53null Saos-2 osteosarcoma cells blocks their proliferation; expression of p53 cancer mutants has no effect (Wassman et al., 2013) (FIG. 5). Importantly, compounds that reactivate p53 cancer mutants specifically block proliferation of Saos-2 cells expressing p53 cancer mutants, but have no effect on growth of p53null cells at the same concentration (FIG. 3). These cell lines are identical except for the p53 cancer mutant, so cell killing (or proliferation arrest) is mediated solely through p53 reactivation.

4.3.2. Assay Results.

FIG. 3AB shows cell growth at the compound concentration with the most significant effect lacking general cell toxicity, as indicated by unaffected growth of p53null cells. Our primary screen is the p53 cancer mutant R175H, which is the single most prevalent human cancer mutation. Active compounds were re-evaluated using an independent cell line expressing a different p53 cancer mutant, G245S. FIG. 3C shows example dose-response curves that indicate inhibition of several p53 cancer mutant cells with much less effect on p53null cells. Many of our compounds reactivate several p53 cancer mutants (FIG. 3CD), which separates our reactivation compounds functionally from the R175H allele-specific NSC319725 and NSC319726 compounds (Yu, et al., 2012) and from the Y220C-specific series of compounds (Basse, et al., 2010; Boeckler, et al., 2008; Wilcken, et al., 2012). FIG. 3E shows micrographs of representative compounds that induced cell death in cells expressing p53 cancer mutants but not p53null cells.

An independent test for p53 cancer mutant reactivation is the well-established transcriptional reporter assay based on p21 and PUMA promoter elements (Wassman, et al., 2013).

As above, the magnitude of reactivated p53-dependent transcription is not considered relevant for a compound's potency in cancer cell killing. Instead, reactivation of transcription is additional evidence that p53 function was restored by the compound. p53-dependent reporter expression was induced by almost all (except 35ZWF) reactivation compounds so far tested (22LSV, 25KKL, 26RQZ, 27WT9, 33AG6, 33BAZ, 35ZWF) within the range observed for the known p53 reactivation molecules PRIMA-1, stictic acid, and NSC-319725 (Wassman et al., 2013) (examples shown in FIG. 3F). Some compounds, including 33BAZ, interfered with the luciferase reporter and needed to be tested by p21 immunoblotting (FIG. 3G).

Together these cell-based experiments (a) confirm the surprising productivity of the identified L1/S3 pocket as a reactivation target, (b) suggest an unexpectedly high "hit rate" of over 10% for our computation-guided p53 reactivation compound discovery strategy, and (c) validate that our computational methods identified novel p53 reactivation compounds.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims.

REFERENCES

The following publications incorporated by reference herein in their entirety:

(Amaro, et al., 2008) Amaro R E, Baron R, McCammon J A. An improved relaxed complex scheme for receptor flexibility in computer-aided drug design. Journal of computer-aided molecular design. 2008; 22(9):693-705. Epub 2008/01/16. doi: 10.1007/s10822-007-9159-2. PubMed PMID: 18196463; PubMed Central PMCID: PMC2516539.

(Amaro & Li, 2010) Amaro R E, Li W W. Emerging methods for ensemble-based virtual screening. Curr Top Med Chem. 2010; 10(1):3-13. Review.

(Baronio, et al., 2010) Baronio R, Danziger S A, Hall L V, Salmon K, Hatfield G W, Lathrop R H, Kaiser P. All-codon scanning identifies p53 cancer rescue mutations. Nucleic Acids Res. 2010 Nov. 1; 38(20):7079-88. Epub 2010 Jun. 25.

(Basse, et al., 2010) Basse N, Kaar J L, Settanni G, Joerger A C, Rutherford T J, Fersht A R. Toward the rational design of p53-stabilizing drugs: probing the surface of the oncogenic Y220C mutant. Chemistry & biology. 2010; 17(1):46-56. Epub 2010/02/10. doi: 10.1016/j.chembiol.2009.12.011. PubMed PMID: 20142040.

(Beraza & Trautwein, 2007) Beraza N, Trautwein C. Restoration of p53 function: a new therapeutic strategy to induce tumor regression? Hepatology. 2007 June; 45(6):1578-9.

(Bichutskiy, et al., 2007) Bichutskiy V Y, Colman R, Brachmann R K, Lathrop R H. Heterogeneous Biomedical Database Integration Using a Hybrid Strategy: A p53 Cancer Research Database. Cancer informatics. 2007; 2:277-87.

(Boeckler, et al., 2008) Boeckler F M, Joerger A C, Jaggi G, Rutherford T J, Veprintsev D B, Fersht A R. Targeted rescue of a destabilized mutant of p53 by an in silico screened drug. Proc Natl Acad Sci USA. 2008 Jul. 29; 105(30):10360-5. Epub 2008 Jul. 23.

(Brown, et al., 2009) Brown C J, Lain S, Verma C S, Fersht A R, Lane D P. Awakening guardian angels: drugging the p53 pathway. Nat Rev Cancer. 2009 December; 9(12):862-73. Review.

(Bykov, et al., 2002) Bykov V J, Issaeva N, Shilov A, Hultcrantz M, Pugacheva E, Chumakov P, Bergman J, Wiman K G, Selivanova G. Restoration of the tumor suppressor function to mutant p53 by a low-molecular-weight compound. Nat Med. 2002 March; 8(3):282-8.

(Bykov, et al., 2005) Bykov V J, Issaeva N, Zache N, Shilov A, Hultcrantz M, Bergman J, Selivanova G, Wiman K G. Reactivation of mutant p53 and induction of apoptosis in human tumor cells by maleimide analogs. J Biol Chem. 2005 Aug. 26; 280(34):30384-91. Epub 2005 Jul. 1.

(Canadillas, et al., 2006) Canadillas J M, Tidow H, Freund S M, Rutherford T J, Ang H C, Fersht A R. Solution structure of p53 core domain: structural basis for its instability. Proc Natl Acad Sci USA. 2006 Feb. 14; 103(7):2109-14. Epub 2006 Feb. 6.

(Canals, et al., 2005) Canals A, Purciolas M, Aymami J, Coll M. The anticancer agent ellipticine unwinds DNA by intercalative binding in an orientation parallel to base pairs. Acta Crystallogr D Biol Crystallogr. 2005 July; 61(Pt 7):1009-12. Epub 2005 Jun. 24.

(Cho, et al., 1994) Cho Y, Gorina S, Jeffrey P D, Pavletich N P. Crystal structure of a p53 tumor suppressor-DNA complex: understanding tumorigenic mutations. Science. 1994 Jul. 15; 265(5170):346-55.

(Danziger, et al., 2006) Danziger S A, Swamidass S J, Zeng J, Dearth L R, Lu Q, Chen J H, Cheng J, Hoang V P, Saigo H, Luo R, Baldi P, Brachmann R K, Lathrop R H. Functional census of mutation sequence spaces: the example of p53 cancer rescue mutants. IEEE/ACM Trans Comput Biol Bioinform. 2006 April-June; 3(2):114-25.

(Danziger, et al., 2007) Danziger S A, Zeng J, Wang Y, Brachmann, R K, Lathrop R H. Choosing where to look next in a mutation sequence space: Active Learning of informative p53 cancer rescue mutants. Bioinformatics. 2007 Jul. 1; 23(13):i104-14.

(Danziger, et al., 2009) Danziger S A, Baronio R, Ho L, Hall L V, Salmon K, Hatfield G W, Kaiser P, Lathrop R H. Predicting positive p53 cancer rescue regions using Most Informative Positive (MIP) active learning. PLoS Comput Biol. 2009 September; 5(9):e1000498. Epub 2008 Sep. 4.

(Daura, et al., 1998) Daura X, Jaun B, Seebach D, van Gunsteren W F, Mark A E. Reversible peptide folding in solution by molecular dynamics simulation. J Mol Biol, 1998. 280(5): p. 925-32.

(Daura, et al., 1999) Daura X G K, Jaun B, Seebach D, van Gunsteren W F, et al. Peptide folding: When simulation meets experiment. Angew Chem-Int Edit. 1999; 38:236-40.

(Demir, et al., 2011) Demir O, Baronio R, Salehi F, Wassman C D, Hall L, Hatfield G W, Chamberlin R, Kaiser P, Lathrop R H, Amaro R E. Ensemble-based computational approach discriminates functional activity of p53 cancer and rescue mutants. PLoS computational biology. 2011; 7(10):e1002238. Epub 2011/10/27. doi: 10.1371/journal.pcbi.1002238. PubMed PMID: 22028641; PubMed Central PMCID: PMC3197647.

(Demma, et al., 2004) Demma M J, Wong S, Maxwell E, Dasmahapatra B. CP-31398 restores DNA-binding activity to mutant p53 in vitro but does not affect p53 homologs p63 and p73. J Biol Chem. 2004 Oct. 29; 279(44):45887-96. Epub 2004 Aug. 11.

(Demma, et al., 2010) Demma M, Maxwell E, Ramos R, Liang L, Li C, Hesk D, Rossman R, Mallams A, Doll R, Liu M, Seidel-Dugan C, Bishop W R, Dasmahapatra B. SCH529074, a small molecule activator of mutant p53, which binds p53 DNA binding domain (DBD), restores growth-suppressive function to mutant p53 and interrupts HDM2-mediated ubiquitination of wild type p53. J Biol Chem. 2010 Apr. 2; 285(14):10198-212. Epub 2010 Feb. 2.

(Durrant, et al., 2010) Durrant J D, Hall L, Swift R V, Landon M, Schnaufer A, Amaro R E. Novel naphthalene-based inhibitors of *Trypanosoma brucei* RNA editing ligase 1. PLoS Negl Trop Dis. 2010 Aug. 24; 4(8):e803.

(Farhat, et al., 2014) Farhat A, Malecki E, Bonaterra G A, Rothlein D, Wolf M, Schmitt J, Rosemeyer H, Kinscherf R. Cytostatic/cytotoxic effects of 5-fluorouridine nucleolipids on colon, hepatocellular, and renal carcinoma cells: in vitro identification of a potential cytotoxic multi-anticancer drug. Chem Biodivers. 2014 March; 11(3): 469-82. doi: 10.1002/cbdv.201300347.

(Fleuret, 2004) Fleuret F. Fast binary feature selection with conditional mutual information. J Mach Learn Res. 2004; 5:1531-55. PubMed PMID: ISI:000236328400005.

(Foster, et al., 1999) Foster B A, Coffey H A, Morin M J, Rastinejad F. Pharmacological rescue of mutant p53 conformation and function. Science. 1999 Dec. 24; 286 (5449):2507-10.

(Friedler, et al., 2002) Friedler A, Hansson L O, Veprintsev D B, Freund S M, Rippin T M, Nikolova P V, Proctor M R, Rüdiger S, Fersht A R. A peptide that binds and stabilizes p53 core domain: chaperone strategy for rescue of oncogenic mutants. Proc Natl Acad Sci USA. 2002 Jan. 22; 99(2):937-42. Epub 2002 Jan. 8.

(Friedler, et al., 2004) Friedler A, DeDecker B S, Freund S M, Blair C, Rüdiger S, Fersht A R. Structural distortion of p53 by the mutation 82495 and its rescue by a designed peptide: implications for "mutant conformation". J Mol Biol. 2004 Feb. 6; 336(1):187-96.

(Garufi, et al., 2013) Garufi A, Trisciuoglio D, Porru M, Leonetti C, Stoppacciaro A, D'Orazi V, Avantaggiati M, Crispini A, Pucci D, D'Orazi G. A fluorescent curcumin-based Zn(II)-complex reactivates mutant (R175H and R273H) p53 in cancer cells. J Exp Clin Cancer Res. 2013 Oct. 7; 32:72. doi: 10.1186/1756-9966-32-72.

(González-Billalabeitia, et al., 2014) Gonzalez-Billalabeitia E, Seitzer N, Song S J, Song M S, Patnaik A, Liu X S, Epping M T, Papa A, Hobbs R M, Chen M, Lunardi A, Ng C, Webster K A, Signoretti S, Loda M, Asara J M, Nardella C, Clohessy J G, Cantley L C, Pandolfi P P. Vulnerabilities of PTEN-TP53-Deficient Prostate Cancers to Compound PARP-PI3K Inhibition. Cancer Discov. 2014 August; 4(8):896-904. doi: 10.1158/2159-8290.CD-13-0230. Epub 2014 May 27.

(Hara, et al., 2006) Hara T, Durell S R, Myers M C, Appella D H. Probing the structural requirements of peptoids that inhibit HDM2-p53 interactions. J Am Chem Soc. 2006 Feb. 15; 128(6): 1995-2004.

(Hess, et al., 2008) Hess B, Kutzner C, van der Spoel D, Lindahl E. GROMACS 4: Algorithms for Highly Efficient, Load-Balanced, and Scalable Molecular Simulation. J Chem Theory Comput 2008; 4(3): 435-447.

(Hock & Vousden, 2012.) Hock A K, Vousden K H. Tumor suppression by p53: fall of the triumvirate? Cell. 2012 Jun. 8; 149(6):1183-5. doi: 10.1016/j.cell.2012.05.024.

(Horvath, Marcou, & Varnek, 2013) Horvath D, Marcou G, Varnek A. Do not hesitate to use Tversky—and other hints for successful active analogue searches with feature count descriptors. Journal of chemical information and modeling. 2013. Epub 2013/06/05. doi: 10.1021/ci400106g. PubMed PMID: 23731338.

(Issaeva, et al., 2003) Issaeva N, Friedler A, Bozko P, Wiman K G, Fersht A R, Selivanova G. Rescue of mutants of the tumor suppressor p53 in cancer cells by a designed peptide. Proc Natl Acad Sci USA. 2003 Nov. 11; 100(23): 13303-7. Epub 2003 Oct. 31.

(Issaeva, et al., 2004) Issaeva N, Bozko P, Enge M, Protopopova M, Verhoef L G, Masucci M, Pramanik A, Selivanova G. Small molecule RITA binds to p53, blocks p53-HDM-2 interaction and activates p53 function in tumors. Nat Med. 2004 December; 10(12):1321-8. Epub 2004 Nov. 21.

(Jain, 2003) Jain A N. Surflex: fully automatic flexible molecular docking using a molecular similarity-based search engine. Journal of medicinal chemistry. 2003; 46(4):499-511. Epub 2003/02/07. doi: 10.1021/jm020406h. PubMed PMID: 12570372.

(Jain, 2007) Jain A N. Surflex-Dock 2.1: robust performance from ligand energetic modeling, ring flexibility, and knowledge-based search. Journal of computer-aided molecular design. 2007; 21(5):281-306. Epub 2007/03/28. doi: 10.1007/s10822-007-9114-2. PubMed PMID: 17387436.

(Kaar, et al., 2010) Kaar J L, Basse N, Joerger A C, Stephens E, Rutherford T J, Fersht A R. Stabilization of mutant p53 via alkylation of cysteines and effects on DNA binding. Protein Sci. 2010 December; 19(12):2267-78. doi: 10.1002/pro.507.

(Karimi, et al., 2010) Karimi M, Conserva F, Mahmoudi S, Bergman J, Wiman K G, Bykov V J. Extract from Asteraceae *Brachylaena ramiflora* induces apoptosis preferentially in mutant p53-expressing human tumor cells. Carcinogenesis. 2010 June; 31(6):1045-53. Epub 2010 Apr. 28.

(Kohn, et al., 1975) Kohn K W, Waring M J, Glaubiger D, Friedman C A. Intercalative binding of ellipticine to DNA. Cancer Res. 1975 January; 35(1):71-6.

(Kravchenko, et al., 2008) Kravchenko J E, Ilyinskaya G V, Komarov P G, Agapova L S, Kochetkov D V, Strom E, Frolova E I, Kovriga I, Gudkov A V, Feinstein E, Chumakov P M. Small-molecule RETRA suppresses mutant p53-bearing cancer cells through a p73 dependent salvage pathway. Proc Natl Acad Sci USA. 2008 Apr. 29; 105 (17):6302-7. Epub 2008 Apr. 18.

(Lambert, et al., 2009) Lambert J M, Gorzov P, Veprintsev D B, Soderqvist M, Segerback D, Bergman J, Fersht A R, Hainaut P, Wiman K G, Bykov V J. PRIMA-1 reactivates mutant p53 by covalent binding to the core domain. Cancer Cell. 2009 May 5; 15(5):376-88.

(Le Guilloux, et al., 2009) Le Guilloux V, Schmidtke P, Tuffery P. Fpocket: an open source platform for ligand pocket detection. BMC Bioinformatics. 2009 Jun. 2; 10:168.

(Li, et al., 2012) Li Tl, Kon N, Jiang L, Tan M, Ludwig T, Zhao Y, Baer R, Gu W. Cell. 2012 Jun. 8; 149(6):1269-83. doi: 10.1016/j.cell.2012.04.026. Tumor suppression in the absence of p53-mediated cell-cycle arrest, apoptosis, and senescence.

(Lindahl, et al., 2001) Lindahl E, Hess B, van der Spoel D. GROMACS 3.0: A package for molecular simulation and trajectory analysis. J Mol Mod, 2001.7: p. 306-317.

(Liu, et al., 2013) Liu X, Wilcken R, Joerger A C, Chuckowree I S, Amin J, Spencer J, Fersht A R. Small molecule induced reactivation of mutant p53 in cancer cells.

Nucleic Acids Res. 2013 Jul. 1; 41(12):6034-44. doi: 10.1093/nar/gkt305. Epub 2013 Apr. 29.

(Malecka, et al., 2009) Malecka K A, Ho W C, Marmorstein R. Crystal structure of a p53 core tetramer bound to DNA. Oncogene. 2009 Jan. 22; 28(3):325-33. Epub 2008 Nov. 3.

(Maslon & Hupp, 2010) Maslon M M, Hupp T R. Drug discovery and mutant p53. Trends Cell Biol. 2010 September; 20(9):542-55. Epub 2010 Jul. 24. Review.

(Metri, et al., 2013) Metri P K, Naz S, Kondaiah P, Prasad K R. MPK-09, a Small Molecule Inspired from Bioactive Styryllactone Restores the Wild-Type Function of Mutant p53. ACS Chem Biol. 2013 Apr. 26. [Epub ahead of print]

(Myers, et al., 2005) Myers M C, Wang J, Iera J A, Bang J K, Hara T, Saito S, Zambetti G P, Appella D H. A new family of small molecules to probe the reactivation of mutant p53. J Am Chem Soc. 2005 May 4; 127(17):6152-3.

(Olivier, et al., 2002) Olivier M, Eeles R, Hollstein M, Khan M A, Harris C C, Hainaut P. The IARC TP53 database: new online mutation analysis and recommendations to users. Hum Mutat. 2002 June; 19(6):607-14.

(Olivier, et al., 2009) Olivier M, Petitjean A, Marcel V, Pare A, Mounawar M, Plymoth A, de Fromentel C C, Hainaut P. Recent advances in p53 research: an interdisciplinary perspective. Cancer Gene Ther. 2009 January; 16(1):1-12. Epub 2008 Sep. 19. Review.

(Oltersdorf, et al., 2005) Oltersdorf T, Elmore S W, Shoemaker A R, Armstrong R C, Augeri D J, Belli B A, Bruncko M, Deckwerth T L, Dinges J, Hajduk P J, Joseph M K, Kitada S, Korsmeyer S J, Kunzer A R, Letai A, Li C, Mitten M J, Nettesheim D G, Ng S, Nimmer P M, O'Connor J M, Oleksijew A, Petros A M, Reed J C, Shen W, Tahir S K, Thompson C B, Tomaselli K J, Wang B, Wendt M D, Zhang H, Fesik S W, Rosenberg S H. An inhibitor of Bcl-2 family proteins induces regression of solid tumours. Nature. 2005 Jun. 2; 435(7042):677-81. Epub 2005 May 15.

(Patel, et al., 2009) Aateka Patel, Stuart A Jones, Albert Ferro, Nilesh Patel. Pharmaceutical salts: a formulation trick or a clinical conundrum? Volume 16, Issue 6. Br J Cardiol; 2009; 16:281-6

(Peltonen, et al., 2010) Peltonen K, Colis L, Liu H, Jäämaa S, Moore H M, Enback J, Laakkonen P, Vaahtokari A, Jones R J, of Hillstrom T M, Laiho M. Identification of novel p53 pathway activating small-molecule compounds reveals unexpected similarities with known therapeutic agents. PLoS One. 2010 Sep. 27; 5(9):e12996.

(Peng, et al., 2003) Peng Y, Li C, Chen L, Sebti S, Chen J. Rescue of mutant p53 transcription function by ellipticine. Oncogene. 2003 Jul. 17; 22(29):4478-87.

(Reddy, et al., 2004) Reddy N L, Hill J, Ye L, Fernandes P B, Stout D M. Identification and structure-activity relationship studies of 3-methylene-2-norbornanone as potent anti-proliferative agents presumably working through p53 mediated apoptosis. Bioorg Med Chem Lett. 2004 Nov. 15; 14(22):5645-9.

(Reha, et al., 2002) Reha D, Kabelác M, Ryjácek F, Sponer J, Sponer J E, Elstner M, Suhai S, Hobza P. Intercalators. 1. Nature of stacking interactions between intercalators (ethidium, daunomycin, ellipticine, and 4',6-diaminide-2-phenylindole) and DNA base pairs. Ab 0 quantum chemical, density functional theory, and empirical potential study. J Am Chem Soc. 2002 Apr. 3; 124(13):3366-76. Erratum in: J Am Chem Soc. 2003 May 7; 125(18) following 5580.

(Rippin, et al., 2002) Rippin T M, Bykov V J, Freund S M, Selivanova G, Wiman K G, Fersht A R. Characterization of the p53-rescue drug CP-31398 in vitro and in living cells. Oncogene. 2002 Mar. 28; 21(14):2119-29.

(Ross, et al., 1978) Ross W E, Glaubiger D L, Kohn K W. Protein-associated DNA breaks in cells treated with adriamycin or ellipticine. Biochim Biophys Acta. 1978 Jun. 22; 519(1):23-30.

(Selivanova, et al., 1997) Selivanova G, Iotsova V, Okan I, Fritsche M, Strom M, Groner B, Grafstrom R C, Wiman K G. Restoration of the growth suppression function of mutant p53 by a synthetic peptide derived from the p53 C-terminal domain. Nat Med. 1997 June; 3(6):632-8.

(Selivanova & Wiman, 2007) Selivanova G, Wiman K G. Reactivation of mutant p53: molecular mechanisms and therapeutic potential. Oncogene. 2007 Apr. 2; 26(15):2243-54.

(Shangary, et al., 2009) Shangary S, Wang S. Small-molecule inhibitors of the MDM2-p53 protein-protein interaction to reactivate p53 function: a novel approach for cancer therapy. Annu Rev Pharmacol Toxicol. 2009; 49:223-41. Review.

(Sharpless & DePinho, 2007) Sharpless N E, DePinho R A. Cancer biology: gone but not forgotten. Nature. 2007 Feb. 8; 445(7128):606-7.

(Soussi & Béroud, 2001) Soussi T, Beroud C. Assessing TP53 status in human tumours to evaluate clinical outcome. Nat Rev Cancer. 2001 December; 1(3):233-40. Review.

(Stoklosa & Goąb, 2005) Stoklosa T, Golab J. Prospects for p53-based cancer therapy. Acta Biochim Pol. 2005; 52(2):321-8.

(Sutherland, et al., 2011) Sutherland H S, Hwang I Y, Marshall E S, Lindsay B S, Denny W A, Gilchrist C, Joseph W R, Greenhalgh D, Richardson E, Kestell P, Ding A, Baguley B C. Therapeutic reactivation of mutant p53 protein by quinazoline derivatives. Invest New Drugs. 2012 October; 30(5):2035-45. doi: 10.1007/s10637-011-9744-z. Epub 2011 Sep. 13.

(Trott & Olson, 2010) Trott O, Olson A J. AutoDock Vina: improving the speed and accuracy of docking with a new scoring function, efficient optimization, and multithreading. J Comput Chem. 2010 Jan. 30; 31(2):455-61.

(Valente, et al., 2013) Valente L J, Gray D H, Michalak E M, Pinon-Hofbauer J, Egle A, Scott C L, Janic A, Strasser A. p53 efficiently suppresses tumor development in the complete absence of its cell-cycle inhibitory and proapoptotic effectors p21, Puma, and Noxa. Cell Rep. 2013 May 30; 3(5):1339-45. doi: 10.1016/j.celrep.2013.04.012. Epub 2013 May 9.

(Vassilev, et al., 2004) Vassilev L T, Vu B T, Graves B, Carvajal D, Podlaski F, Filipovic Z, Kong N, Kammlott U, Lukacs C, Klein C, Fotouhi N, Liu E A. In vivo activation of the p53 pathway by small-molecule antagonists of MDM2. Science. 2004 Feb. 6; 303(5659):844-8. Epub 2004 Jan. 2.

(Ventura, et al., 2007) Ventura A, Kirsch D G, McLaughlin M E, Tuveson D A, Grimm J, Lintault L, Newman J, Reczek E E, Weissleder R, Jacks T. Restoration of p53 function leads to tumour regression in vivo. Nature. 2007 Feb. 8; 445(7128):661-5. Epub 2007 Jan. 24.

(Wang, et al., 2005) Wang Y, Hailey J, Williams D, Wang Y, Lipari P, Malkowski M, Wang X, Xie L, Li G, Saha D, Ling W L, Cannon-Carlson S, Greenberg R, Ramos R A, Shields R, Presta L, Brams P, Bishop W R, Pachter J A. Inhibition of insulin-like growth factor-I receptor (IGF- IR) signaling and tumor cell growth by a fully human neutralizing anti-IGF-IR antibody. Mol Cancer Ther. 2005 August; 4(8):1214-21.

(Wang & El-Deiry, 2008) Wang W, El-Deiry W S. Restoration of p53 to limit tumor growth. Curr Opin Oncol. 2008 January; 20(1):90-6. Review.

(Wang, et al., 2009) Wang Y, Xiao J, Suzek T O, Zhang J, Wang J, Bryant S H. PubChem: a public information system for analyzing bioactivities of small molecules. Nucleic acids research. 2009; 37(Web Server issue): W623-33. Epub 2009/06/06. doi: 10.1093/nar/gkp456. PubMed PMID: 19498078; PubMed Central PMCID: PMC2703903.

(Wassman, et al., 2013) Wassman C D, Baronio R, Demir O, Wallentine B D, Chen C K, Hall L V, Salehi F, Lin D W, Chung B P, Hatfield G W, Richard Chamberlin A, Luecke H, Lathrop R H, Kaiser P, Amaro R E. Computational identification of a transiently open L1/S3 pocket for reactivation of mutant p53. Nat Commun. 2013; 4:1407. Epub 2013/01/31. doi: 10.1038/ncomms2361.

(Weinmann, et al., 2008) Weinmann L, Wischhusen J, Demma M J, Naumann U, Roth P, Dasmahapatra B, Weller M. A novel p53 rescue compound induces p53-dependent growth arrest and sensitises glioma cells to Apo2L/TRAIL-induced apoptosis. Cell Death Differ. 2008 April; 15(4):718-29. doi: 10.1038/sj.cdd.4402301. Epub 2008 Jan. 18.

(Wilcken, et al., 2012) Wilcken R, Liu X, Zimmermann M O, Rutherford T J, Fersht A R, Joerger A C, Boeckler F M. Halogen-Enriched Fragment Libraries as Leads for Drug Rescue of Mutant p53. Journal of the American Chemical Society. 2012; 134(15):6810-8. Epub 2012/03/24. doi: 10.1021/ja301056a. PubMed PMID: 22439615.

(Wiman, 2007) Wiman K G. Restoration of wild-type p53 function in human tumors: strategies for efficient cancer therapy. Adv Cancer Res. 2007; 97:321-38. Review.

(Witten & Frank, 2005) Witten I H, Frank E. Data mining: practical machine learning tools and techniques with Java implementations. 2nd ed: Morgan Kaufmann, San Francisco; 2005.

(Xue, et al., 2007) Xue W, Zender L, Miething C, Dickins R A, Hernando E, Krizhanovsky V, Cordon-Cardo C, Lowe SW. Senescence and tumour clearance is triggered by p53 restoration in murine liver carcinomas. Nature. 2007 Feb. 8; 445(7128):656-60. Epub 2007 Jan. 24.

(Yu, et al., 2102) Yu, X., Vazquez, A., Levine, A. J. & Carpizo, D. R. Allele-Specific p53 Mutant Reactivation. Cancer cell 21, 614-625 (2012).

(Zache, et al., 2008) Zache N, Lambert J M, Rokaeus N, Shen J, Hainaut P, Bergman J, Wiman K G, Bykov V J. Mutant p53 targeting by the low molecular weight compound STIMA-1. Mol Oncol. 2008 June; 2(1):70-80. Epub 2008 Mar. 7.

(Zhao, et al., 2010a) Zhao C Y, Szekely L, Bao W, Selivanova G. Rescue of p53 function by small-molecule RITA in cervical carcinoma by blocking E6-mediated degradation. Cancer Res. 2010 Apr. 15; 70(8):3372-81.

(Zhao, et al., 2010b) Zhao C Y, Grinkevich V V, Nikulenkov F, Bao W, Selivanova G. Rescue of the apoptotic-inducing function of mutant p53 by small molecule RITA. Cell Cycle. 2010 May; 9(9):1847-55. Epub 2010 May 15.

What is claimed is:

1. A method of enhancing p53 activity of a p53 mutant polypeptide, comprising directly interacting the p53 mutant polypeptide with at least one compound, or a tautomer or pharmaceutically acceptable salt thereof, wherein the at least one compound is selected from the group consisting of:

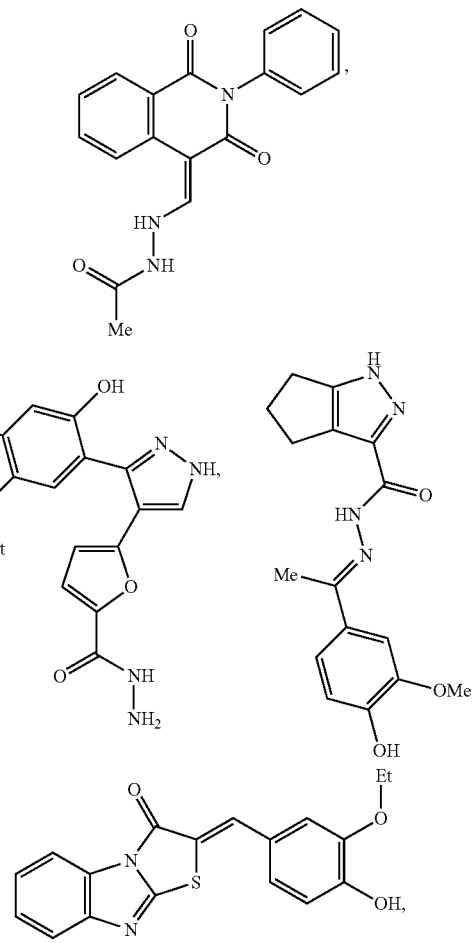

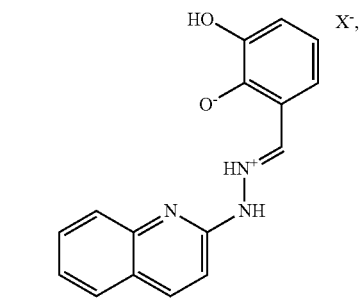

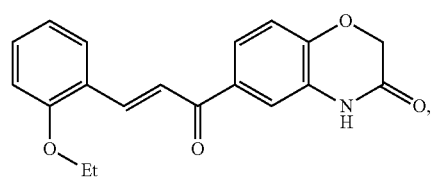

-continued
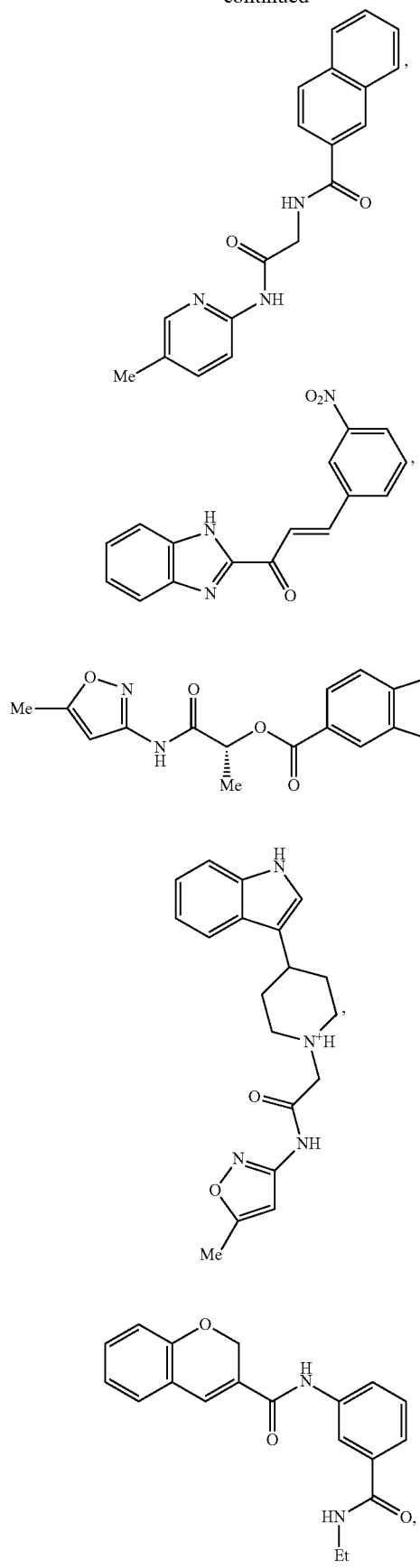
-continued
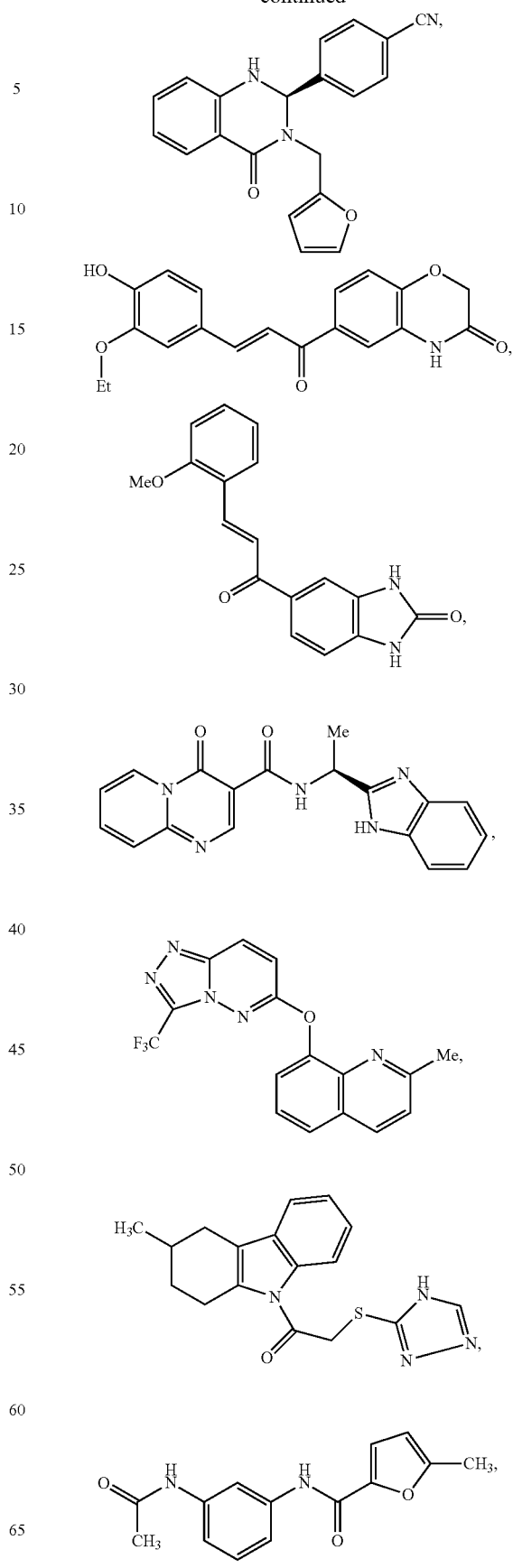

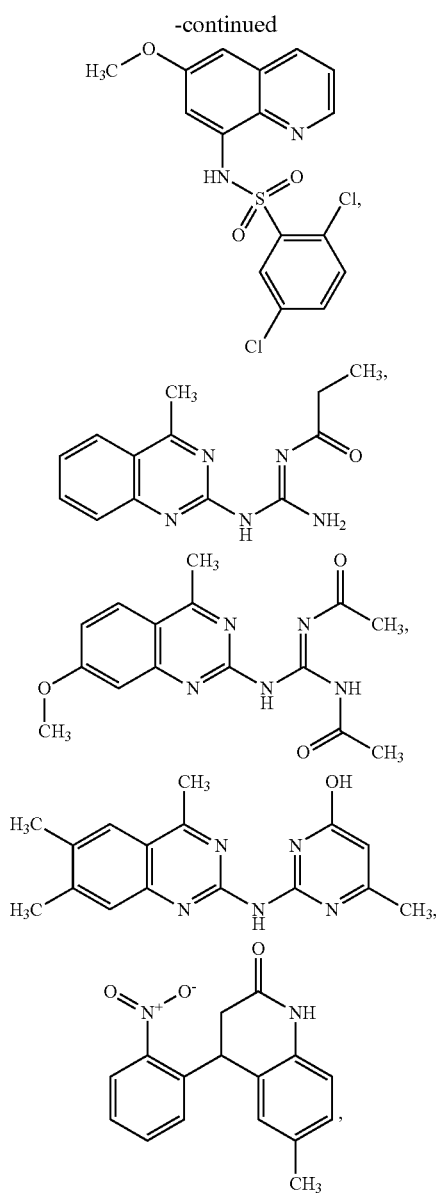
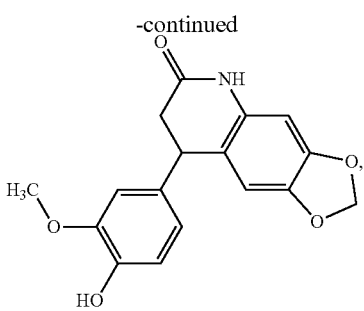
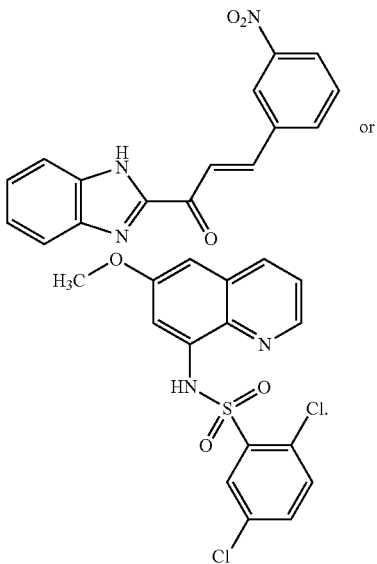
and a combination thereof,
wherein X⁻ is a counterion, and the p53 activity of the p53 mutant polypeptide is enhanced in the presence of the at least one compound as compared to its absence.
2. The method of claim 1, wherein the at least one compound is one of the following compounds, or a combination thereof:
* * * * *

UNITED STATES PATENT AND TRADEMARK OFFICE
CERTIFICATE OF CORRECTION

PATENT NO. : 9,737,546 B2  
APPLICATION NO. : 14/910976  
DATED : August 22, 2017  
INVENTOR(S) : Amaro et al.

Page 1 of 1

It is certified that error appears in the above-identified patent and that said Letters Patent is hereby corrected as shown below:

On the Title Page

Item (72) Inventors, "Salehi-Amin" should read -- Salehi-Amiri --

Signed and Sealed this
Seventh Day of November, 2017

Joseph Matal
*Performing the Functions and Duties of the*
*Under Secretary of Commerce for Intellectual Property and*
*Director of the United States Patent and Trademark Office*